(12) United States Patent
Wondka et al.

(10) Patent No.: US 8,776,793 B2
(45) Date of Patent: Jul. 15, 2014

(54) METHODS AND DEVICES FOR SENSING RESPIRATION AND CONTROLLING VENTILATOR FUNCTIONS

(75) Inventors: Anthony D. Wondka, Thousand Oaks, CA (US); Robert F. Bryan, San Ramon, CA (US); Mark McCall, Berkeley, CA (US); Cuong Q. Tran, Danville, CA (US)

(73) Assignee: Breathe Technologies, Inc., Irvine, CA (US)

( * ) Notice: Subject to any disclaimer, the term of this patent is extended or adjusted under 35 U.S.C. 154(b) by 681 days.

(21) Appl. No.: 12/988,477

(22) PCT Filed: Apr. 17, 2009

(86) PCT No.: PCT/US2009/041027
§ 371 (c)(1), (2), (4) Date: May 4, 2011

(87) PCT Pub. No.: WO2009/151791
PCT Pub. Date: Dec. 17, 2009

(65) Prior Publication Data
US 2011/0197885 A1   Aug. 18, 2011

Related U.S. Application Data

(60) Provisional application No. 61/071,252, filed on Apr. 18, 2008.

(51) Int. Cl.
| | | |
|---|---|---|
| *A61M 11/00* | (2006.01) | |
| *A61B 5/087* | (2006.01) | |
| *A61M 16/04* | (2006.01) | |
| *A61M 16/00* | (2006.01) | |
| *A61B 5/03* | (2006.01) | |
| *A61B 5/085* | (2006.01) | |

(52) U.S. Cl.
CPC .............. *A61M 16/00* (2013.01); *A61B 5/087* (2013.01); *A61B 5/085* (2013.01); *A61M 16/0465* (2013.01); *A61M 2205/17* (2013.01); *A61B 5/03* (2013.01); *A61M 2016/0015* (2013.01)
USPC ............. 128/204.23; 128/204.21; 128/207.14

(58) Field of Classification Search
USPC .......................... 128/204.18–204.23, 207.14
See application file for complete search history.

(56) References Cited

U.S. PATENT DOCUMENTS

| 50,641 A | 10/1865 | Stone |
|---|---|---|
| 428,592 A | 5/1890 | Chapman |

(Continued)

FOREIGN PATENT DOCUMENTS

| DE | 19626924 | 1/1998 |
|---|---|---|
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Steven Douglas
(74) *Attorney, Agent, or Firm* — Stetina Brunda Garred & Brucker

(57) ABSTRACT

Improved methods and devices are described for sensing the respiration pattern of a patient and controlling ventilator functions, particularly for use in an open ventilation system. A ventilation and breath sensing apparatus may include a ventilation gas delivery circuit and a ventilation tube coupled to the ventilation gas delivery circuit. A plurality of pressure sensing elements may be separated by a distance and may produce independent signals. The signals may be used to detect pressure differentials between the plurality of pressure sensing elements. Sensing ports may be located in an airway, and connected to transducers that are valved to optimize sensitivity and overpressure protection. Airway pressure and flow can both be obtained and used to optimize ventilator synchronization and therapy.

30 Claims, 22 Drawing Sheets

(56) References Cited

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |

(56) References Cited

U.S. PATENT DOCUMENTS

| | | | |
|---|---|---|---|
| 4,938,212 | A | 7/1990 | Snook et al. |
| 4,944,310 | A | 7/1990 | Sullivan |
| 4,967,743 | A | 11/1990 | Lambert |
| 4,971,049 | A | 11/1990 | Rotariu et al. |
| 4,982,735 | A | 1/1991 | Yagata et al. |
| 4,986,269 | A | 1/1991 | Hakkinen |
| 4,989,599 | A | 2/1991 | Carter |
| 4,990,157 | A | 2/1991 | Roberts et al. |
| 5,000,175 | A | 3/1991 | Pue |
| 5,002,050 | A | 3/1991 | McGinnis |
| 5,005,570 | A | 4/1991 | Perkins |
| 5,018,519 | A | 5/1991 | Brown |
| 5,022,394 | A | 6/1991 | Chmielinski |
| 5,024,219 | A | 6/1991 | Dietz |
| 5,025,805 | A | 6/1991 | Nutter |
| 5,038,771 | A | 8/1991 | Dietz |
| 5,042,478 | A | 8/1991 | Kopala et al. |
| 5,046,491 | A | 9/1991 | Derrick |
| 5,046,492 | A | 9/1991 | Stackhouse et al. |
| 5,048,515 | A | 9/1991 | Sanso |
| 5,048,516 | A | 9/1991 | Soderberg |
| 5,052,400 | A | 10/1991 | Dietz |
| 5,054,484 | A | 10/1991 | Hebeler, Jr. |
| 5,058,580 | A | 10/1991 | Hazard |
| 5,074,299 | A | 12/1991 | Dietz |
| 5,076,267 | A | 12/1991 | Pasternack |
| 5,090,408 | A | 2/1992 | Spofford et al. |
| 5,097,827 | A | 3/1992 | Izumi |
| 5,099,836 | A | 3/1992 | Rowland et al. |
| 5,099,837 | A | 3/1992 | Russel, Sr. et al. |
| 5,101,820 | A | 4/1992 | Christopher |
| 5,103,815 | A | 4/1992 | Siegel et al. |
| 5,105,807 | A | 4/1992 | Kahn et al. |
| 5,107,830 | A | 4/1992 | Younes |
| 5,107,831 | A | 4/1992 | Halpern et al. |
| 5,113,857 | A | 5/1992 | Dickerman et al. |
| 5,117,818 | A | 6/1992 | Palfy |
| 5,117,819 | A | 6/1992 | Servidio et al. |
| 5,127,400 | A | 7/1992 | DeVries et al. |
| 5,134,995 | A | 8/1992 | Gruenke et al. |
| 5,134,996 | A | 8/1992 | Bell |
| 5,140,045 | A | 8/1992 | Askanazi et al. |
| 5,148,802 | A | 9/1992 | Sanders et al. |
| 5,161,525 | A | 11/1992 | Kimm et al. |
| 5,165,397 | A | 11/1992 | Arp |
| 5,181,509 | A | 1/1993 | Spofford et al. |
| 5,184,610 | A | 2/1993 | Marten et al. |
| 5,186,167 | A | 2/1993 | Kolobow |
| 5,193,532 | A | 3/1993 | Moa et al. |
| 5,193,533 | A | 3/1993 | Body et al. |
| 5,199,424 | A | 4/1993 | Sullivan et al. |
| 5,211,170 | A | 5/1993 | Press |
| 5,217,008 | A | 6/1993 | Lindholm |
| 5,233,978 | A | 8/1993 | Callaway |
| 5,233,979 | A | 8/1993 | Strickland |
| 5,239,994 | A | 8/1993 | Atkins |
| 5,239,995 | A | 8/1993 | Estes et al. |
| 5,243,972 | A | 9/1993 | Huang |
| 5,245,995 | A | 9/1993 | Sullivan et al. |
| 5,255,675 | A | 10/1993 | Kolobow |
| 5,258,027 | A | 11/1993 | Berghaus |
| 5,269,296 | A | 12/1993 | Landis |
| 5,271,388 | A | 12/1993 | Whitwam et al. |
| 5,271,391 | A | 12/1993 | Graves |
| 5,275,159 | A | 1/1994 | Griebel |
| 5,279,288 | A | 1/1994 | Christopher |
| 5,287,852 | A | 2/1994 | Arkinstall |
| 5,303,698 | A | 4/1994 | Tobia et al. |
| 5,303,700 | A | 4/1994 | Weismann et al. |
| 5,318,019 | A | 6/1994 | Celaya |
| 5,331,995 | A | 7/1994 | Westfall et al. |
| 5,335,656 | A | 8/1994 | Bowe et al. |
| 5,339,809 | A | 8/1994 | Beck, Jr. et al. |
| 5,349,946 | A | 9/1994 | McComb |
| 5,368,017 | A | 11/1994 | Sorenson et al. |
| 5,370,112 | A | 12/1994 | Perkins |
| 5,373,842 | A | 12/1994 | Olsson et al. |
| 5,375,593 | A | 12/1994 | Press |
| 5,388,575 | A | 2/1995 | Taube |
| 5,394,870 | A | 3/1995 | Johansson |
| 5,398,676 | A | 3/1995 | Press et al. |
| 5,398,682 | A | 3/1995 | Lynn |
| 5,400,778 | A | 3/1995 | Jonson et al. |
| 5,419,314 | A | 5/1995 | Christopher |
| 5,438,979 | A | 8/1995 | Johnson, Jr. et al. |
| 5,438,980 | A | 8/1995 | Phillips |
| 5,443,075 | A | 8/1995 | Holscher |
| 5,460,174 | A | 10/1995 | Chang |
| 5,460,613 | A | 10/1995 | Ulrich et al. |
| 5,474,062 | A | 12/1995 | DeVires et al. |
| 5,477,852 | A | 12/1995 | Landis et al. |
| 5,485,850 | A | 1/1996 | Dietz |
| 5,490,502 | A | 2/1996 | Rapoport et al. |
| 5,503,146 | A | 4/1996 | Froehlich et al. |
| 5,503,497 | A | 4/1996 | Dudley et al. |
| 5,507,282 | A | 4/1996 | Younes |
| 5,509,409 | A | 4/1996 | Weatherholt |
| 5,513,628 | A | 5/1996 | Coles et al. |
| 5,513,631 | A | 5/1996 | McWilliams |
| 5,513,635 | A | 5/1996 | Bedi |
| 5,522,382 | A | 6/1996 | Sullivan et al. |
| 5,526,806 | A | 6/1996 | Sansoni |
| 5,529,060 | A | 6/1996 | Salmon et al. |
| 5,533,506 | A | 7/1996 | Wood |
| 5,535,738 | A | 7/1996 | Estes et al. |
| 5,537,997 | A | 7/1996 | Mechlenburg et al. |
| 5,538,002 | A | 7/1996 | Boussignac et al. |
| 5,542,415 | A | 8/1996 | Brody |
| 5,546,935 | A | 8/1996 | Champeau |
| 5,549,106 | A | 8/1996 | Gruenke et al. |
| 5,551,419 | A | 9/1996 | Froehlich et al. |
| 5,558,086 | A | 9/1996 | Smith et al. |
| 5,564,416 | A | 10/1996 | Jones |
| 5,575,282 | A | 11/1996 | Knoch et al. |
| 5,582,164 | A | 12/1996 | Sanders |
| 5,593,143 | A | 1/1997 | Ferrarin |
| 5,595,174 | A | 1/1997 | Gwaltney |
| 5,598,837 | A | 2/1997 | Sirianne, Jr. et al. |
| 5,598,840 | A | 2/1997 | lund et al. |
| 5,603,315 | A | 2/1997 | Sasso, Jr. |
| 5,605,148 | A | 2/1997 | Jones |
| 5,626,131 | A | 5/1997 | Chua et al. |
| 5,632,269 | A | 5/1997 | Zdrojkowski |
| 5,636,630 | A | 6/1997 | Miller et al. |
| 5,645,053 | A | 7/1997 | Remmers et al. |
| 5,645,054 | A | 7/1997 | Cotner et al. |
| 5,647,351 | A | 7/1997 | Weismann et al. |
| 5,669,377 | A | 9/1997 | Fenn |
| 5,669,380 | A | 9/1997 | Garry et al. |
| 5,676,132 | A | 10/1997 | Tillotson et al. |
| 5,676,135 | A | 10/1997 | McClean |
| 5,682,878 | A | 11/1997 | Ogden |
| 5,682,881 | A | 11/1997 | Winthrop et al. |
| 5,687,713 | A | 11/1997 | Bahr et al. |
| 5,687,714 | A | 11/1997 | Kolobow et al. |
| 5,687,715 | A | 11/1997 | Landis et al. |
| 5,690,097 | A | 11/1997 | Howard et al. |
| 5,692,497 | A | 12/1997 | Schnitzer et al. |
| 5,697,364 | A | 12/1997 | Chua et al. |
| 5,704,345 | A | 1/1998 | Berthon-Jones |
| 5,711,296 | A | 1/1998 | Kolobow |
| 5,715,812 | A | 2/1998 | Deighan et al. |
| 5,715,815 | A | 2/1998 | Lorenzen et al. |
| 5,720,278 | A | 2/1998 | Lachmann et al. |
| 5,735,268 | A | 4/1998 | Chua et al. |
| 5,735,272 | A | 4/1998 | Dillon et al. |
| 5,740,796 | A | 4/1998 | Skog |
| 5,752,511 | A | 5/1998 | Simmons et al. |
| 5,762,638 | A | 6/1998 | Shikani et al. |
| 5,791,337 | A | 8/1998 | Coles et al. |
| 5,819,723 | A | 10/1998 | Joseph |
| 5,826,579 | A | 10/1998 | Remmers et al. |
| 5,845,636 | A | 12/1998 | Gruenke et al. |
| 5,865,173 | A | 2/1999 | Froehlich |

(56) References Cited

U.S. PATENT DOCUMENTS

| | | |
|---|---|---|
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |

(56) References Cited

U.S. PATENT DOCUMENTS

| | | |
|---|---|---|
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Ström |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Büscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Schöller et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |

(56) References Cited

U.S. PATENT DOCUMENTS

| | | |
|---|---|---|
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham, Deceased et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy, Jr. |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |

(56) References Cited

U.S. PATENT DOCUMENTS

| | | |
|---|---|---|
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunaratnam et al. |
| 2008/0092905 A1 | 4/2008 | Gunaratnam et al. |
| 2008/0092906 A1 | 4/2008 | Gunaratnam et al. |
| 2008/0099024 A1 | 5/2008 | Gunaratnam et al. |
| 2008/0099027 A1 | 5/2008 | Gunaratnam et al. |
| 2008/0105264 A1 | 5/2008 | Gunaratnam et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |

(56) References Cited

U.S. PATENT DOCUMENTS

| | | |
|---|---|---|
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | Mcauley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |

(56) References Cited

FOREIGN PATENT DOCUMENTS

| WO | WO-2010/150187 | 12/2010 |
|----|----------------|---------|
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiners Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiners Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiners Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiners Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiners Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, *Ex Parte Quayle* Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care,* 1992: 37(8), pp. 918-922.
"ATS Statement: Guidelines for the Six-Minute Walk Test," *Am. J. Respir. Crit. Care Med.,* 2002: 166, pp. 111-117.
"Passy-Muir Speaking Valves," *Respiratory,* Nov. 13, 1998, 7 pages.
Ambrosino, "Exercise and noninvasive ventilatory support," *Monaldi Arch Chest Dis.,* 2000: 55(3): 242-246.
Ambrosino, "Weaning and Respiratory Muscle Dysfunction: The Egg Chicken Dilemma," *Chest,* 2005: 128(2), pp. 481-483.
Bach et al., "Intermittent Positive Pressure Ventilation via Nasal Access in the Management of Respiratory Insufficiency," *Chest,* 1987: 92(1), pp. 168-170.
Banner et al., "Extubating at a Pressure Support Ventilation Level Corresponding to Zero Imposed Work of Breathing," *Anesthesiology,* Sep. 1994: 81(3A), p. A271.
Banner et al., "Imposed Work of Breathing and Methods of Triggering a Demand-Flow, Continuous Positive Airway Pressure System," *Critical Care Medicine,* 1993: 21(2), pp. 183-190.
Banner et al., "Site of Pressure Measurement During Spontaneous Breathing with Continuous Positive Airway Pressure: Effect on Calculating Imposed Work of Breathing," Critical Care Medicine, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.,* 2007: 2(4), pp. 585-591.
Barreiro et al., "Noninvasive ventilation," *Crit Care Clin.,* 2007; 23(2): 201-22.
Bauer et al., "ADAM Nasal CPAP Circuit Adaptation: A Case Report," *Sleep,* 1991: 14(3), pp. 272-273.
Blanch, "Clinical Studies of Tracheal Gas Insufflation," *Resp. Care,* 2001: 45(2), pp. 158-166.

(56) References Cited

OTHER PUBLICATIONS

Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," Chest, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," Resp. Care, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," Resp. Care, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," Thorax, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
Macinryre, "Long-Term Oxygen Therapy: Conference Summary," *Resp. Care*, 2000: 45(2), pp. 237-245.
Macintyre et al., "Acute exacerbations and repiratory failure in chronic obstructive pulmonary disease," *Proc. Am. Thorac. Soc.*, 2008: 5(4), pp. 530-535.

Massie et al., "Clinical Outcomes Related to Interface Type in Patients With Obstructive Sleep Apnea/Hypopnea Syndrome Who Are Using Continuous Positive Airway Pressure," Chest, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," Chest, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," Chest, 1995: vol. 108(2), pp. 509-514.
Mettey, "Use of CPAP Nasal Cannula for Aids of the Newborns in Tropical Countries," Medecine Tropicale, 1985: 45(1), pp. 87-90.
Nahmias et al., "Treatment of the Obstructive Sleep Apnea Syndrome Using a Nasopharyngeal Tube", Chest, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," Chest, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," Chest, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.).
Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," Chest, 1983: 83(1), pp. 144-145.
Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.
Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," Chest, 1990: 97, pp. 364-368.
Tsuboi et al., "Ventilatory Support During Exercise in Patients With Pulmonary Tuberculosis Sequelae," Chest, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.

(56) References Cited

OTHER PUBLICATIONS

Wijkstra et al., "Nocturnal non-invasive positive pressure ventilation for stable chronic obstructive pulmonary disease," *Cochrane Database Syst. Rev.*, 2002, 3: 1-22.
Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker' Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in co-pending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.

SECTION D-D

SECTION E-E

DETAIL H

SECTION G-G

SECTION G'-G'

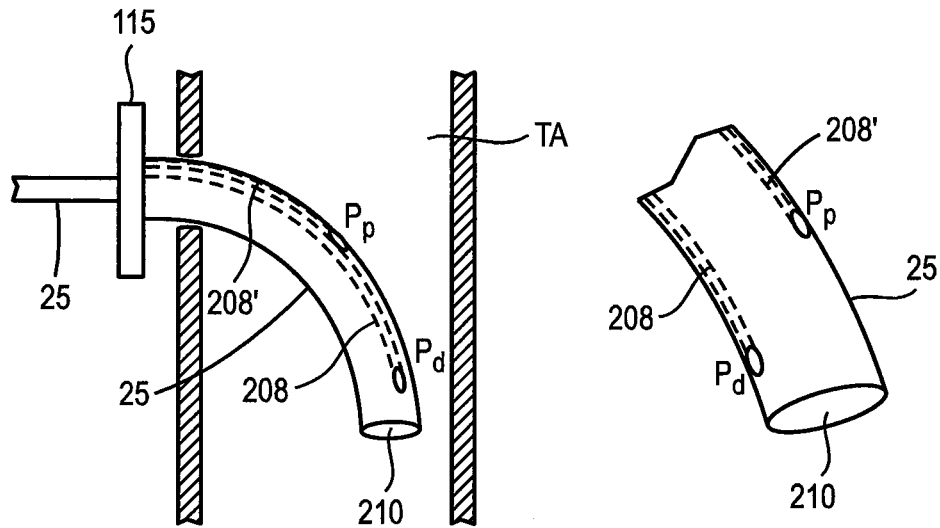
FIG. 17  FIG. 17A
FIG. 18
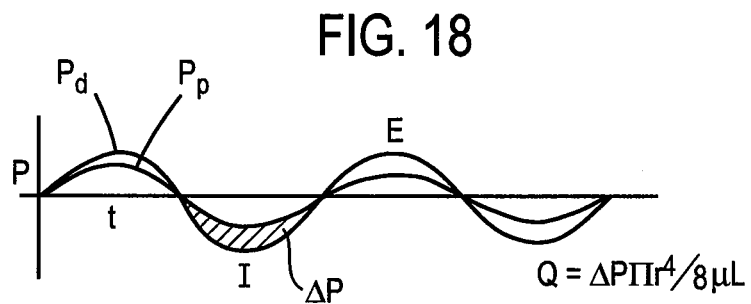
$Q = \Delta P \Pi r^4 / 8\mu L$
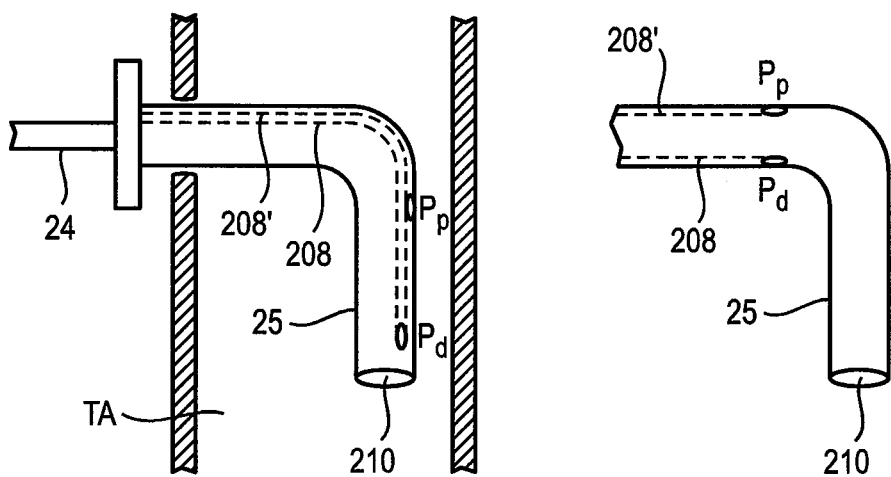
FIG. 19  FIG. 19A

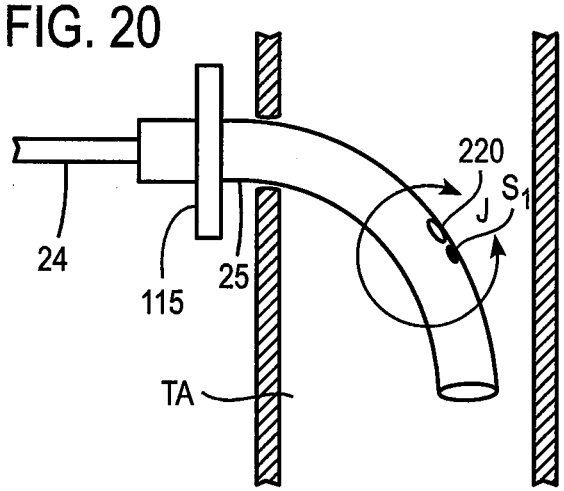
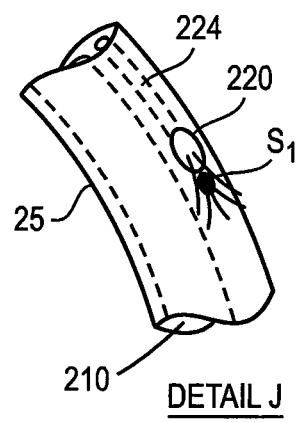
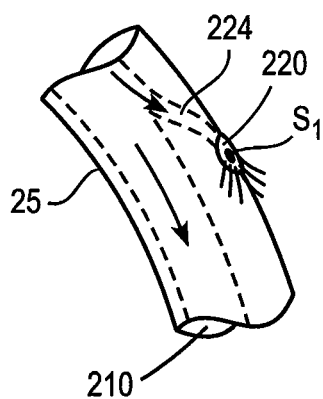
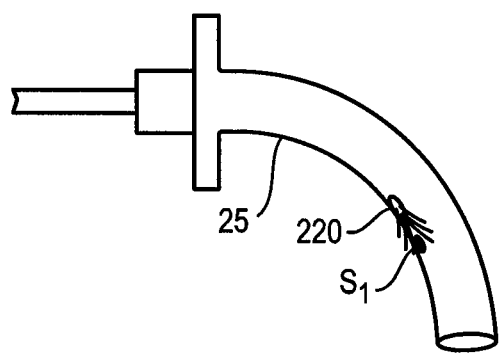
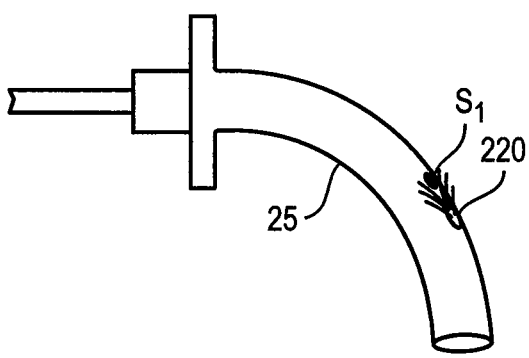

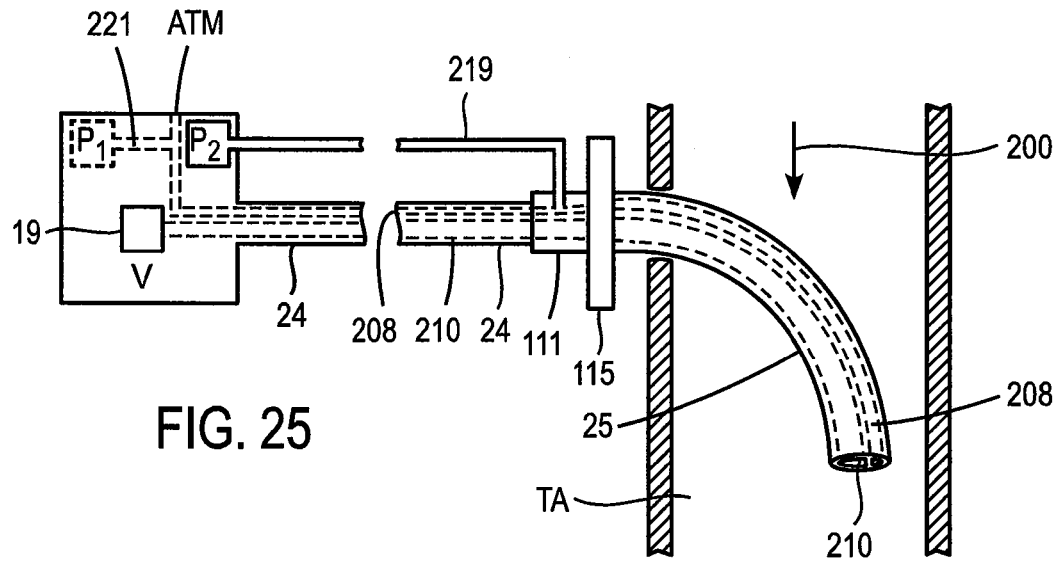
FIG. 25
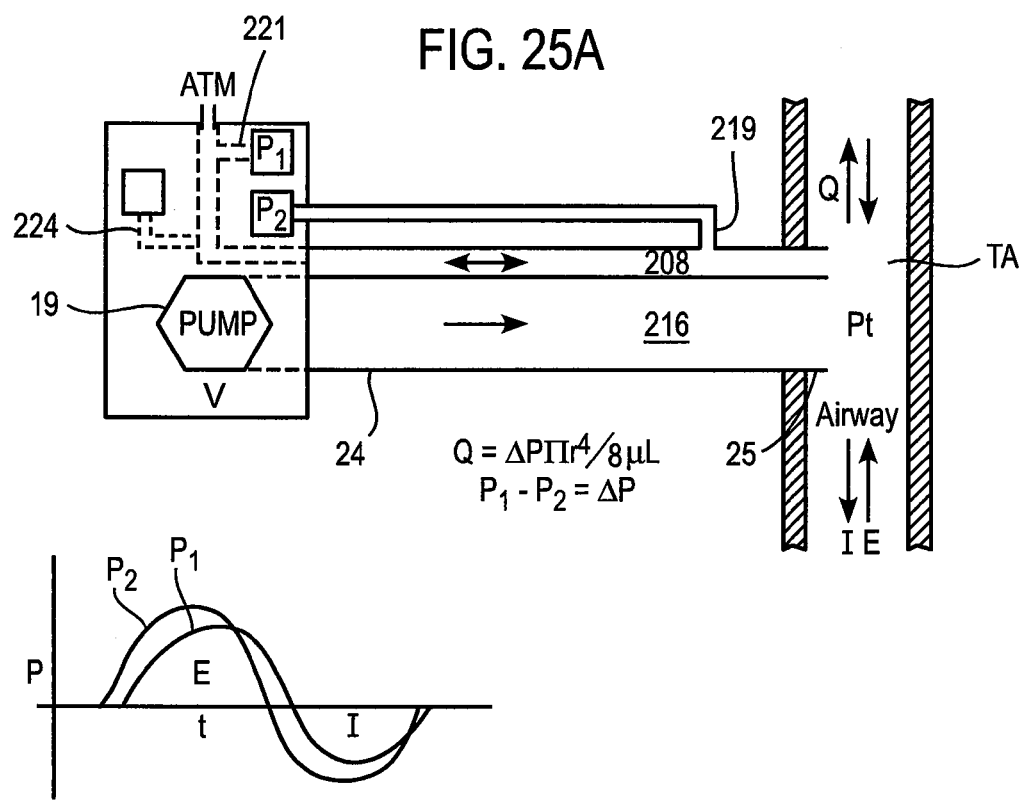
FIG. 25A
FIG. 25B

DETAIL B

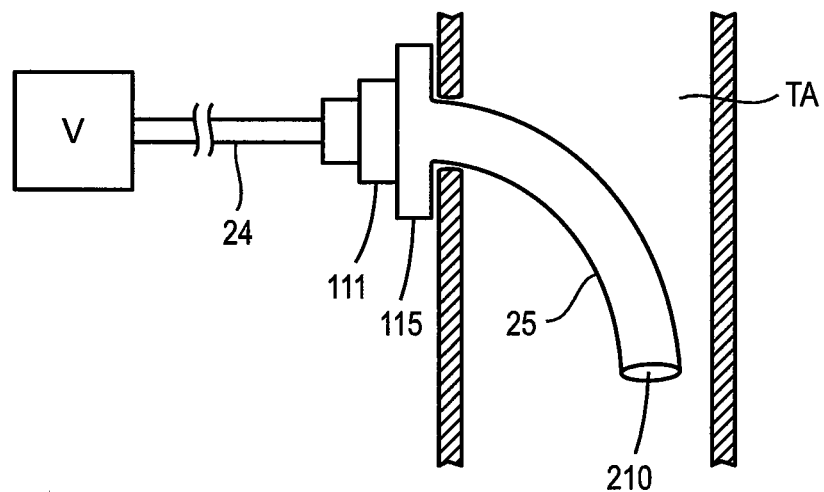
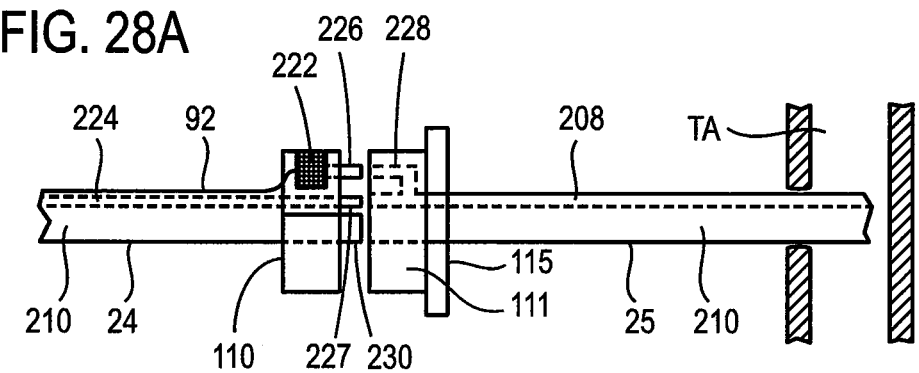
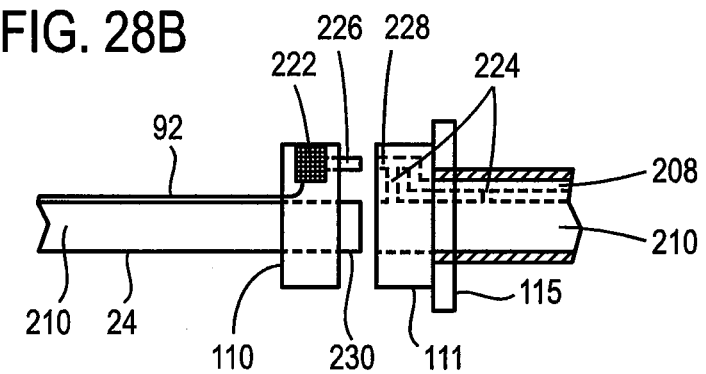

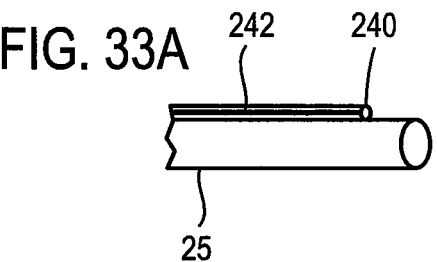
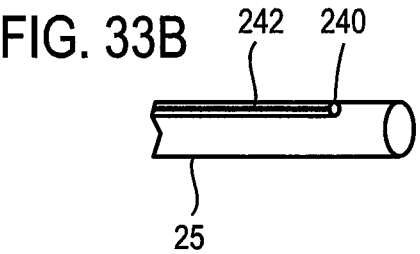
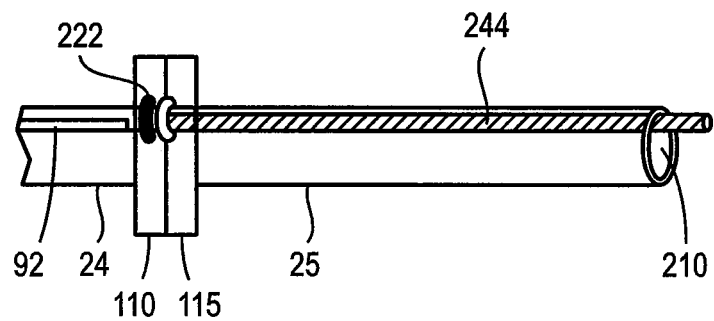
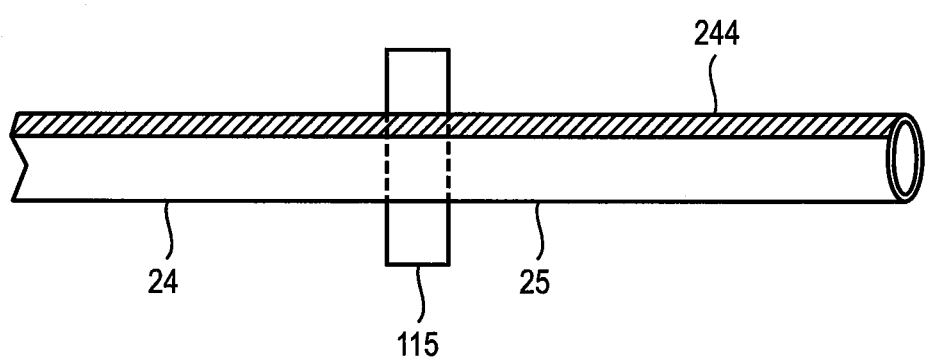
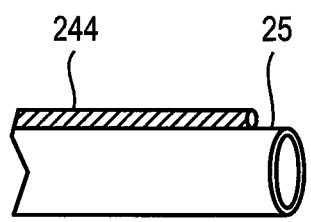

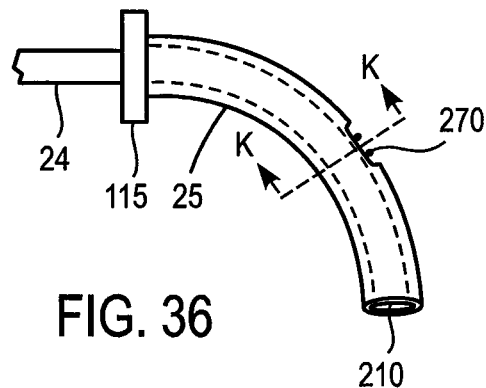
FIG. 36
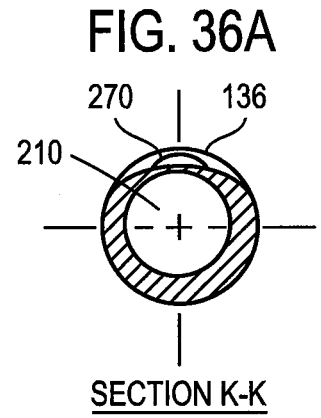
FIG. 36A
SECTION K-K
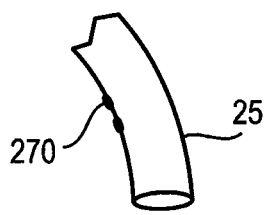
FIG. 36B
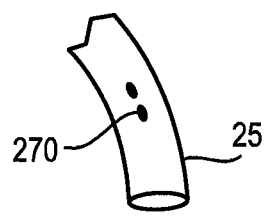
FIG. 36C
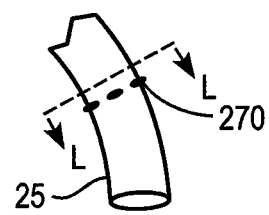
FIG. 36D
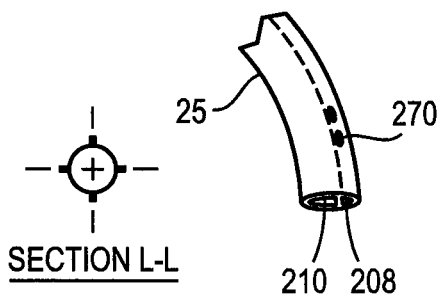
FIG. 36F
SECTION L-L
FIG. 36E
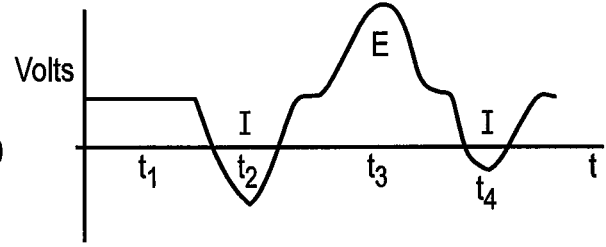
FIG. 37
FIG. 37A
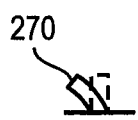
FIG. 37B
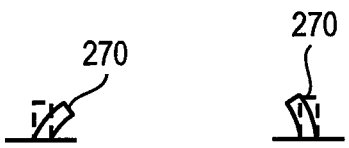
FIG. 37C
FIG. 37D

METHODS AND DEVICES FOR SENSING RESPIRATION AND CONTROLLING VENTILATOR FUNCTIONS

CROSS-REFERENCE TO RELATED APPLICATIONS

This application claims priority to U.S. Provisional Patent Application No. 61/071,252, entitled "Methods and Devices for Sensing Respiration and Controlling Ventilator Functions", filed Apr. 18, 2008, the content of which is incorporated by reference in its entirety.

This application incorporates by reference in their entireties: U.S. patent application Ser. No. 10/870,849, entitled "Methods, Systems and Devices for Improving Ventilation in a Lung Area", filed Jun. 17, 2004; U.S. patent application Ser. No. 12/153,423, entitled "Methods and Devices for Sensing Respiration and Providing Ventilation Therapy", filed May 19, 2008; U.S. patent application Ser. No. 10/771,803, entitled "Method and Arrangement for Respiratory Support for a Patient Airway Prosthesis and Catheter", filed Feb. 4, 2004; U.S. patent application Ser. No. 11/523,518, entitled "Systems, Methods and Apparatus for Respiratory Support of a Patient", filed Sep. 20, 2006; and U.S. patent application Ser. No. 11/523,519, entitled "Systems, Methods and Apparatus for Respiratory Support of a Patient", filed Sep. 20, 2006.

FIELD OF THE INVENTION

The present invention relates to ventilation therapy for persons requiring respiratory support from a ventilator. Conditions can include respiratory impairment and breathing disorders, such as chronic obstructive pulmonary disease (COPD), pulmonary fibrosis, acute respiratory distress syndrome (ARDS), neuromuscular impairment, and sleep apnea, or anesthesia, emergency and the like. The present invention relates more specifically to measuring a patient's respiratory pattern using breath sensing approaches, and using that measured information from breath sensors to synchronize ventilator output to a breathing pattern of a patient.

BACKGROUND OF THE INVENTION

There are two general types of control systems for conventional ventilators. A first type delivers gas to a patient based on a frequency selected by the clinician that is independent of patient activity. This control system is used when the patient is non-alert, sedated, unresponsive or paralyzed. In this type of system, the ventilator is breathing for the patient. A second type of control system delivers gas to the patient in response to an inspiratory effort created by the patient. This type of ventilation helps the patient breathe. There are also ventilators and modes of ventilation that combine these two types of control systems. The present invention relates to ventilation systems and modes that respond to an inspiratory effort by the patient.

Control systems that respond to patient breathing efforts require breath sensors to detect inspiration. Conventional systems use pressure or flow sensors to detect the start of an inspiratory effort by the patient. The sensor is located somewhere in-line with the ventilation gas delivery circuit, either inside the ventilator, or in the tubing between the ventilator and the patient, or at the patient end of the tubing. In-line breath sensors are also used to measure the entire respiratory curve in addition to just the start of inspiration; however, because the gas being delivered by the ventilator also moves past the sensor, the sensor during that time no longer measures the patient's respiration but rather the ventilator activity. In a closed ventilation system, the patient lung pressure and the gas delivery circuit pressure, while not necessarily identical, are typically very close. In an open ventilation system in which the patient is also spontaneously breathing, the patient lung pressure and the gas delivery circuit pressure can be very different. In this case, a breath sensor in-line with the ventilation gas delivery circuit can be ineffective in measuring the entire respiratory pattern.

In ventilation systems in which the patient is expected to be breathing or partially breathing spontaneously, synchronization between the ventilator and the patient is important for comfort and efficacy. However, poor synchrony is still reported in some cases because of the demanding and exacting task of measuring all the different possible spontaneous breathing signals and the vast range of variations that exist.

Some attempts have been made to use sensors that are in parallel with the ventilation gas delivery system and are more directly coupled to the patient's actual respiration. The intent of these systems is to improve breath detection, to improve responsiveness of the ventilator, to improve the synchrony of the ventilator to the patient, or to reduce work of breathing required for a patient to trigger the ventilator.

For example, chest impedance sensors can be used to measure the entire respiratory curve of a patient and to use that signal to control the ventilator and synchronize the ventilator to the patient's breathing. However, this approach is technically challenging because the signal is prone to drift, noise and artifacts caused by patient motion and abdominal movement. In another technology, the neural respiratory drive measured with an esophageal catheter is used to measure the respiration of a patient. However, this technique requires an additional invasive device and sensor, and does not monitor exhalation activity since that is a neurally passive function.

Thermal intra-airway breath sensing is promising because it directly measures airflow in the trachea and, if implemented correctly, can determine the complete breathing pattern of the patient and can generate a breathing signal that is not disrupted by the ventilator gas flow.

Pressure-based breath sensing in the airway measures pressure at the distal end of an endotracheal tube, and using that pressure measurement to control a ventilator function for the purpose of reducing the patient's breath effort required for the patient to trigger a mechanical breath from the ventilator. Reduction in effort is a result of a quicker response time of the pressure signal because of the proximity of the signal to the patient's lung. While an improvement over conventional triggering techniques in conventional ventilation, this technique still has disadvantages and in fact has not yet been converted into commercial practice. For example, a sensor must have the necessary sensitivity and accuracy to detect light breathing pressures, while also withstanding high pressures so that it does not fail during a high pressure condition, such as a cough. This is especially of concern in medium and higher pressure ventilation delivery systems. Further, additional information related to the respiration pattern is desirable to increase the efficacy of the therapy. Also, existing systems have a logistically cumbersome interface with the external control system. In summary, existing systems have the one or more of the following disadvantages that require improvement: (1) they do not measure the complete breath cycle, (2) the are in-line with the channel used for ventilation gas delivery, (3) they have a limited range of accuracy and sensitivity, and (4) they are logistically cumbersome to interface with the ventilator.

SUMMARY OF THE INVENTION

The current invention is an improvement over existing breath sensing techniques. The invention may include pressure-based breath sensing methods and systems that may be in parallel with the ventilation circuit. The methods and systems may measure intra-tracheal breathing pressures or nasal or oral breathing pressures, and may be in series or in-line with airflow in a patient airway.

Various techniques for intra-airway pressure-based breath sensing are described in the present invention. In an exemplary embodiment, a system includes a multichannel, multi-transducer breath sensing arrangement is described. The system is capable of measuring pressure throughout a wide range, while maintaining the necessary resolution at low pressures, by intelligently switching between channels. In an exemplary embodiment, a system includes means to measure or derive intra-tracheal flow or nasal or oral air flow. In an exemplary embodiment, a system includes positioning of a transducer close to the patient on the patient interface. In an exemplary embodiment, other types of pressure or flow sensing technologies are described.

Improved methods and devices are described for sensing the respiration pattern of a patient and controlling ventilator functions, particularly for use in an open ventilation system. A ventilation and breath sensing apparatus may include a ventilation gas delivery circuit and a ventilation tube coupled to the ventilation gas delivery circuit. A plurality of pressure sensing elements may be separated by a distance and may produce independent signals. The signals may be used to detect pressure differentials between the plurality of pressure sensing elements.

In certain embodiments, a ventilation and breath sensing method and apparatus may use two intra-airway sensing systems, a thermal sensor for measuring tracheal, nasal or oral airflow and a pressure sensor for measuring tracheal pressure, and wherein the tracheal airflow signal is used to derive breathing flow rate and breathing volume. The pressure and flow signals may be used to determine compliance, resistance and an approximation for work of breathing. In exemplary embodiments, a ventilation and breath sensing method and apparatus may use two pressure sensing lumens terminating in the airway, the ports of which are separated by a distance to create a pressure differential between the two signals, thereby obtaining both tracheal pressure and tracheal airflow. A ventilation and breath sensing method and apparatus may use an intra-airway sensor and a flush lumen and flush port in the delivery tube to maintain a contamination-free sensor. A ventilation and breath sensing method and apparatus may use an intra-airway sensor and a flush lumen connected to the main ventilation gas delivery lumen to maintain a contamination-free sensor. A ventilation and breath sensing method and apparatus may use a pressure sensor mounted in the stomal flange or connector of the ventilation catheter, pneumatically communicating with the airway through the stoma via an extension tube extending transcutaneously into the airway. A ventilation and breath sensing method and apparatus may use a two section system, an external section including a pressure sensor, and an inserted section with a breath sensing lumen, the pressure sensor pneumatically communicating with the sensing lumen when the two sections are connected, and a flush lumen included in the external section connecting to the sensing lumen when the two sections are connected. The sensing lumen may be flushed via an interconnecting channel with the ventilator gas delivery lumen. A ventilation and breath sensing method and apparatus may be used in which a ventilation catheter is placed into a outer sleeve, such as a tracheostomy tube or stomal guide, with a heat moisture exchanger, bacterial filter, breathing port, intra-airway spontaneous breath sensors, and an inspiratory valve positioned in the annular space between the catheter and outer sleeve, and optionally a expiratory relief valve. A ventilation and breath sensing method and apparatus with a tracheal airflow conduit may be positioned in the airway for measuring tracheal airflow with sensors positioned in the airflow conduit to measure tracheal breathing pressure and conduit airflow, wherein the conduit airflow is used to derive tracheal breathing flow rate. A ventilation and breath sensing method and apparatus may be used in which a spontaneous breathing lumen separate from the ventilator gas delivery lumen extends into the airway and includes multiple pressure taps connecting to the lumen, to measure a pressure drop across the pressure taps, and the pressure drop correlated to tracheal airflow, and the pressure tap closest to the patient used to measure patient ventilation pressure. A ventilation and breath sensing method and apparatus may use a pressure sensor mounted in the stomal flange of the ventilation catheter or outer tube around the ventilation catheter, pneumatically communicating with a lumen in the catheter which extends to the airway, with the catheter placed in a sleeve such as a tracheostomy tube. A ventilation and breath sensing method and apparatus may use a pressure sensor mounted in the flange or connector of a ventilation catheter, with a sensing extension tube connected to the pressure sensor, where the catheter is placed inside an outer sleeve such as a tracheostomy tube. The outer sleeve may be a stomal sleeve, guide or stent. The pressure transducer may be positioned near a neck flange. The pressure transducer signal may be transmitted wirelessly. A ventilation and breath sensing method and apparatus may be used in which an array of three pressure sensors may be used to measure spontaneous breathing, airway lung pressure and ventilation gas delivery pressure, where at least one pressure sensor senses pressure in a transtracheal sensing lumen, and at lest one pressure sensor sense pressure in the ventilation gas delivery circuit. One pressure sensor in the ventilation gas delivery circuit may be disabled during ventilator gas delivery. A ventilation and breath sensing method and apparatus may include a gas delivery circuit with a sensing lumen, and an outer sleeve such as a tracheostomy tube with a sensing lumen, and with pneumatic coupling between the gas delivery circuit and outer sleeve such that the gas delivery circuit sensing lumen taps into the outer sleeve sensing lumen. A ventilation and breath sensing method and apparatus may include a two piece ventilation interface in which a ventilation catheter is placed in a thin wall small diameter profile outer sleeve, such as a thin walled small diameter profile tracheostomy tube which includes a tight to shaft cuff when deflated and a stomal spacer, for the purpose of reducing resistance to upper airway breathing. A ventilation and breath sensing method and apparatus may include two sections in which an inserted disposable ventilation catheter section receives an external reusable gas delivery section, in which a sensor is positioned near the connector of the external section and connects to a sensing lumen of the inserted section. A ventilation and breath sensing method and apparatus may include three sections, a pressure transducer, a gas delivery circuit, and a ventilation tube, in which a reusable pressure transducer is attached to the flange of the gas delivery circuit or ventilation catheter, and when attached plugs into a receiving port that communicates with a sensing lumen extending into the airway. A ventilation and breath sensing method and apparatus may include a ventilation delivery cannula with an array of sensing lumens in the wall of the delivery cannula extrusion, and with a plurality of ports connecting the sensing lumens with the space outside the cannula, in order to provide multiple sites of pressure sensing in the airway. A ventilation and breath sensing method and apparatus may use two pressure sensing elements or ports with a physical screen between the elements to dampen the signal response time and amplitude of relative to the direction of flow. A ventilation and breath sensing method and apparatus may use two sensing elements on the inferior and superior aspects of the delivery cannula to create a physical barrier to bias the response time of each element that correlates to the direction of flow. A ventilation and breath sensing method and apparatus may use a fiber optic sensor positioned on a portion of the catheter residing in the airway. A ventilation and breath sensing method and apparatus may use a fiber optic sensor positioned on a reusable portion of the ventilation catheter, communicating with a catheter lumen extending into the airway. A ventilation and breath sensing method and apparatus may use a liquid filled sensing lumen to transmit the pressure signal from the airway to the transducer. A ventilation and breath sensing method and apparatus may use a strain gauge or array of strain gauges, measuring direction and amplitude of strain of the gauge, to determine flow direction, speed and amplitude. The sensing lumen may be placed on the posterior aspect of the ventilation catheter, on the anterior aspect of the ventilation catheter, on the superior aspect of the ventilation catheter, on the inferior aspect of the ventilation catheter, on the lateral aspect of the ventilation catheter, on the multiple locations or aspects of the ventilation catheter, or on the posterior aspect of the ventilation catheter. The sensing lumen may terminate beyond the tip of the ventilation tube or at a location recessed from the tip of the ventilation tube. The flow and pressure data may be used to determine airway resistance, lung compliance and an estimate of work of breathing. A ventilation tube may be placed into the airway and may include a sensing lumen, a flush port, fenestrations, and an inflatable cuff. The ventilation tube may include an inflatable and deflatable cuff, and at least two sensing lumens with one lumen terminating distal to the cuff and one lumen terminating proximal to the cuff, wherein the pressures of the two sensing lumens are compared to provide an indication of the degree of obstruction being caused by the cuff.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE INVENTION

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 17 shows breath sensing using two pressure sensing lumens terminating in the airway, the ports of which are separated by a distance to create a pressure differential between the two signals, thereby obtaining both tracheal pressure and tracheal airflow.

FIG. 17A shows an alternative to FIG. 17 in which two pressure sensing ports are placed on opposite surfaces on the ventilation tube.

FIG. 18 shows resultant pressure signals from system of FIG. 17.

FIG. 19 shows an alternate shape of the delivery cannula from that of FIG. 17 in which the two pressure sensing lumen ports are positioned on a straight section of cannula and positioned parallel to the patient's breath airflow path.

FIG. 19A shows an alternative to FIG. 19 in which two pressure sensing ports are placed on a straight section of ventilation tube on opposite surfaces of the ventilation tube, orthogonal to the direction of breathing airflow.

FIG. 20 shows breath sensing using an intra-airway sensor and a flush lumen and flush port in the delivery tube to maintain a contamination-free sensor.

FIG. 20A describes in more detail the flush lumen and flush port of FIG. 20.

FIG. 21 shows breath sensing using an intra-airway sensor and a flush lumen connected to the main ventilation gas delivery lumen to maintain a contamination-free sensor.

FIG. 22A show an alternate configuration of a flush port from that described in FIG. 20 with the flush port located on the anterior or inferior surface of the cannula.

FIG. 22B shows an alternate configuration of a flush port from that described in FIG. 20 in which the flush media is directed retrograde at the sensor.

Figure 23A:
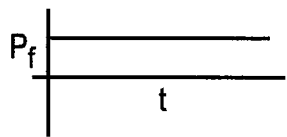

FIG. 23A shows a graphical description of a constant steady state flushing pressure profile.

Figure 23B:
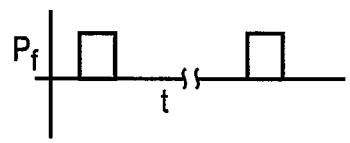

FIG. 23B shows a graphical description of an intermittent flushing pressure profile in which flushing occurs as needed or intermittently.

Figure 23C:
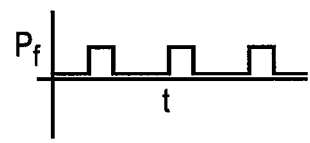

FIG. 23C shows a graphical description of a cyclical flushing pressure profile, optionally in synchrony with the patient's respiration pattern.

Figure 24:
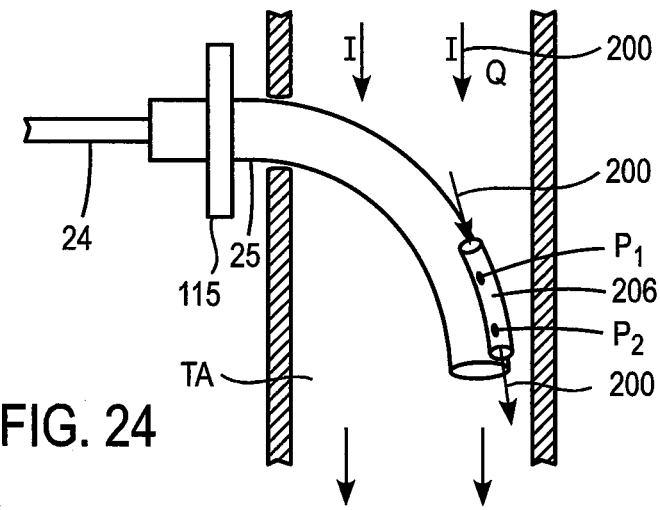

FIG. 24 shows a ventilation and breath sensing system with a tracheal airflow conduit positioned in the airway for measuring tracheal airflow.

Figure 24A:
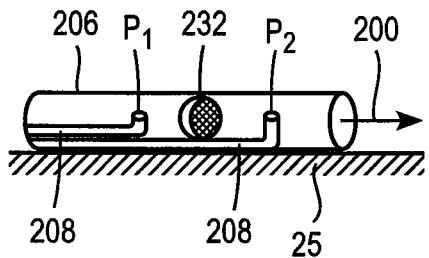

FIG. 24A shows a ventilation and breath sensing system with two pressure sensors or pressure sensing ports in the flow conduit and separated by a flow conduit screen.

FIG. 25 shows a ventilation and breath sensing system in which a spontaneous breathing lumen extends into the airway and including multiple pressure taps connecting to the lumen, to measure a pressure drop that can be correlated to tracheal airflow.

FIG. 25A shows a schematic cross section of the system of FIG. 25.

FIG. 25B shows a resultant pressure sensing signals and derivation of delta P for determination of tracheal airflow from the system described in FIG. 25.

Figure 26:
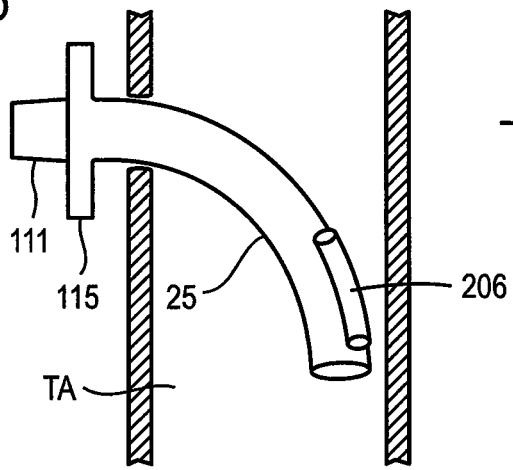

FIG. 26 shows a ventilation interface and sensing system with a ventilation tube and flow conduit on the ventilation tube to obtain flow rate readings.

Figure 26A:
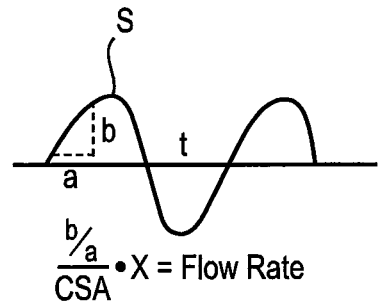

FIG. 26A shows a graphical representation of the sensor signal of the sensor shown in FIG. 26, indicating how the signal is correlated to flow rate.

Figure 27:
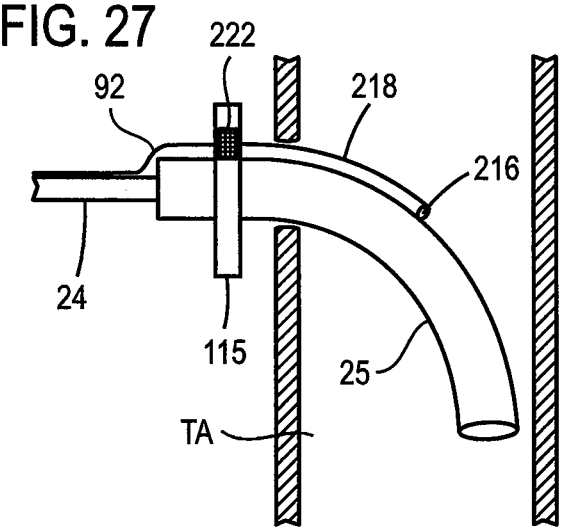

FIG. 27 shows breath sensing using a pressure sensor mounted in the stomal flange of the ventilation catheter, pneumatically communicating with the airway through the stoma via an extension tube extending transcutaneously into the airway.

Figure 27A:
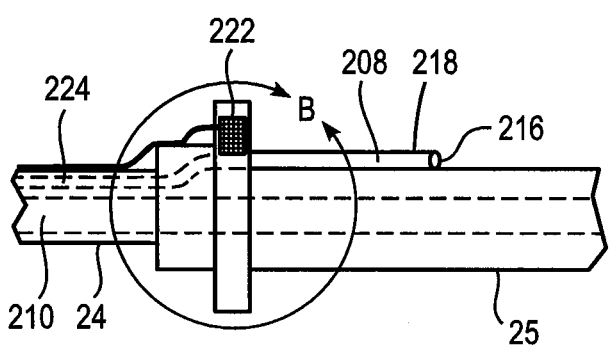

FIG. 27A shows a schematic cross section of FIG. 27.

Figure 27B:
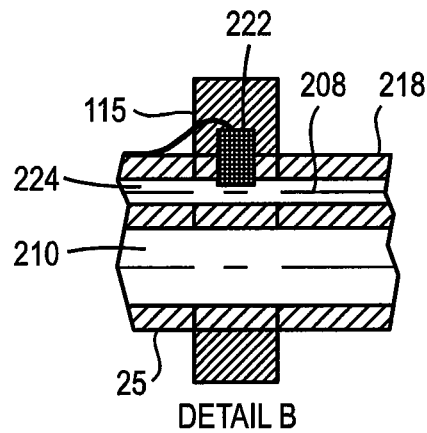

FIG. 27B shows a detail of FIG. 27A.

FIG. 28 shows a ventilation gas delivery and breath sensing using a two section system, an external section including a pressure sensor mounted in proximal connector of the ventilation catheter, and an inserted section with a breath sensing lumen, the pressure sensor pneumatically communicating with the sensing lumen when the two sections are connected, and a flush lumen included in the external section connecting to the sensing lumen when the two sections are connected.

FIG. 28A shows a cross section schematic of system in FIG. 28.

FIG. 28B shows a cross section of alternate configuration of FIG. 28, where the sensing lumen is flushed via an interconnecting channel with the ventilator gas delivery lumen.

Figure 29:
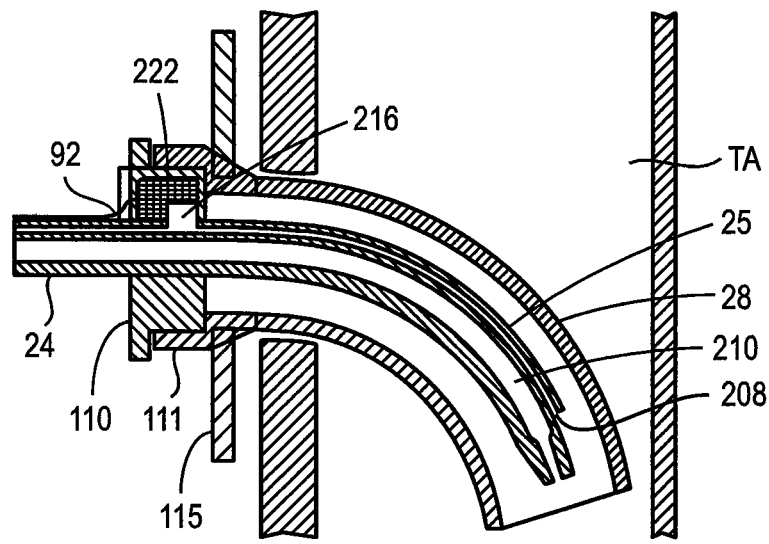

FIG. 29 shows a ventilation and breath sensing using a pressure sensor mounted in the stomal flange of the ventilation catheter, pneumatically communicating with a lumen in the catheter which extends to the airway, with the catheter placed in a sleeve such as a tracheostomy tube.

Figure 30:
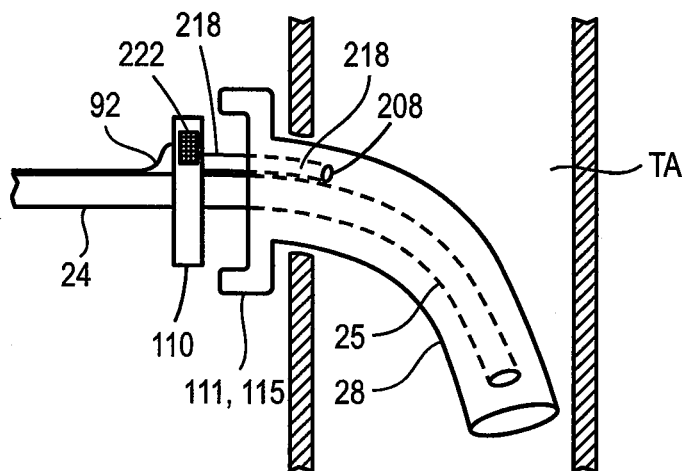

FIG. 30 shows a ventilation and breath sensing system using a pressure sensor mounted in the flange or connector of a ventilation catheter, with a sensing extension tube connected to the pressure sensor, where the catheter is placed inside an outer sleeve such as a tracheostomy tube.

Figure 30A:
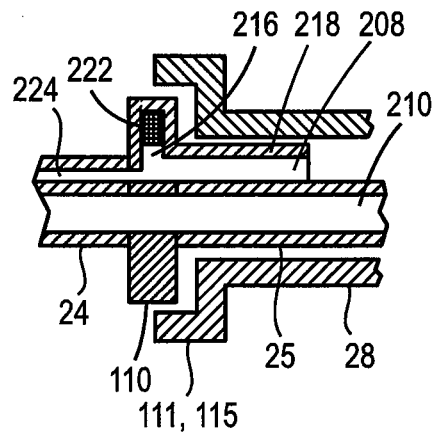

FIG. 30A shows a detailed cross sectional view of system of FIG. 30.

Figure 31:
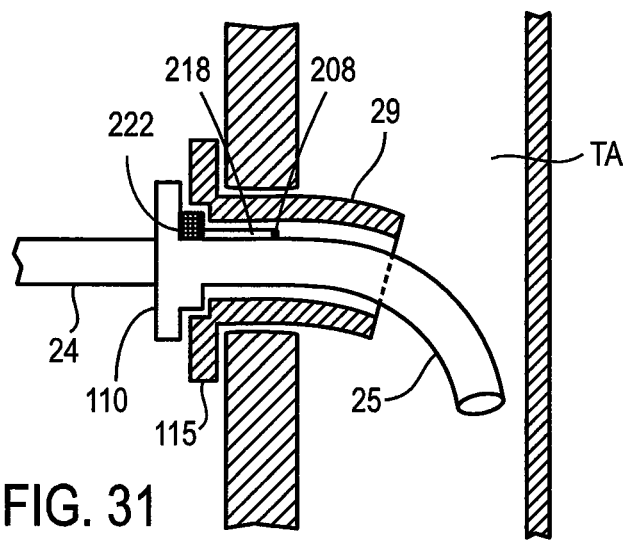

FIG. 31 shows the system of FIG. 30 where the outer sleeve is a stomal sleeve, guide or stent.

Figure 32:
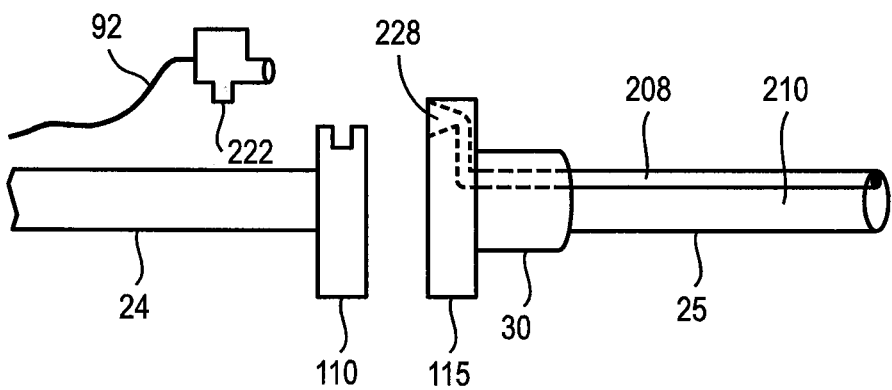

FIG. 32 shows a two or three piece ventilation interface and sensing system in which a reusable pressure transducer is attached to the flange of the ventilation catheter or gas delivery tube, and when attached plugs into a receiving port that communicates with a sensing lumen extending into the airway.

Figure 33:
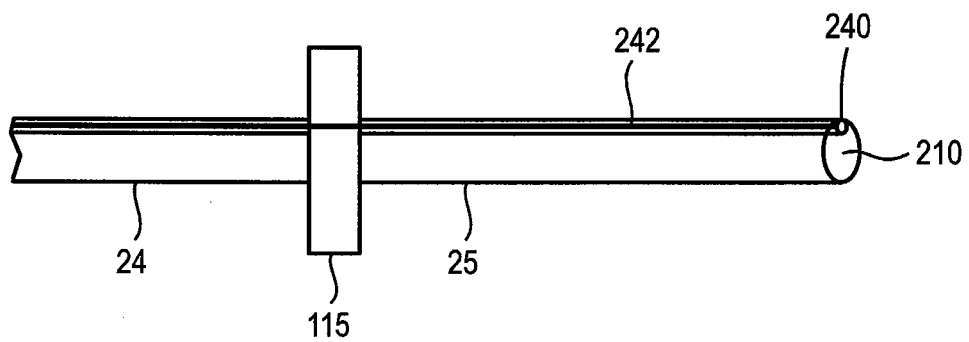

FIG. 33 shows breath sensing using a fiber optic sensor positioned on a portion of the catheter residing in the airway.

FIG. 33A shows an alternative to FIG. 33 in which the sensor tip is recessed from the tip of the catheter and is on the outside of the catheter.

FIG. 33B shows an alternative to FIG. 33 in which the sensor tip is recessed from the tip of the catheter and is on the inside of the catheter.

FIG. 34 shows breath sensing using a fiber optic sensor positioned on a reusable portion of the ventilation catheter, communicating with a catheter lumen extending into the airway.

FIG. 35 shows breath sensing using a liquid filled sensing lumen to transmit the pressure signal from the airway to the transducer.

FIG. 35A shows an alternative to FIG. 35 in which the tip of the sensing lumen is recessed from the tip of the catheter.

FIG. 36 shows breath sensing using a strain gauge or array of strain gauges, measuring direction and amplitude of strain of the gauge, to determine flow direction, speed and amplitude.

FIG. 36A shows a cross section through the catheter of FIG. 36 at line K-K.

FIG. 36B shows an alternate location of the sensors of FIG. 36, with the sensors on the anterior or inferior side of the catheter.

FIG. 36C shows an alternate location of the sensors of FIG. 36 in which the sensors are located on a lateral side of the catheter.

FIG. 36D shows an alternate location of the sensors of FIG. 36 in which the sensors are positioned circumferentially around the surface of the catheter.

FIG. 36E shows a cross section of FIG. 36d at line L-L.

FIG. 36F shows an alternate location of the sensors of FIG. 36 in which the sensors are positioned inside a sensing lumen which is integral to the ventilation cannula or catheter.

FIG. 37 shows graphical tracing of the strain gauge signal of the system of FIG. 36.

FIG. 37A shows the resting state of the strain gauge during no flow corresponding to breath phases of signal of FIG. 37.

FIG. 37B shows the deflected state of the strain gauge during inspiration corresponding to breath phases of signal of FIG. 37.

FIG. 37C shows the deflected state of the strain gauge during exhalation corresponding to breath phases of signal of FIG. 37.

FIG. 37D shows the deflected state of the strain gauge during inspiration, corresponding to breath phases of signal of FIG. 37.

Figure 38A:
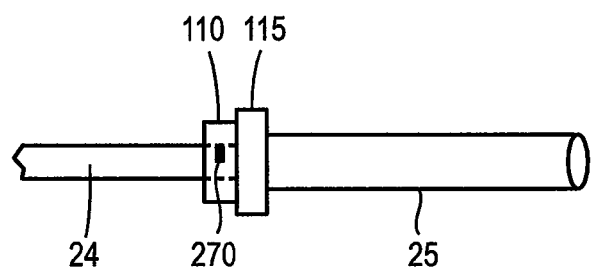

FIG. 38A shows an alternate location of strain gauges of the system described in FIG. 36 in which the gauge is located at a connector positioned outside of an airway.

Figure 38B:
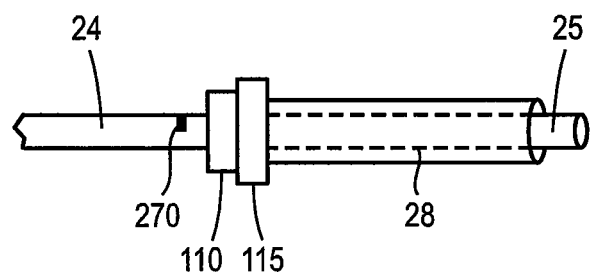

FIG. 38B shows an alternate location of strain gauges of the system described in FIG. 36 in which the gauge is located in a ventilation circuit or cannula outside of an airway.

Figure 38C:
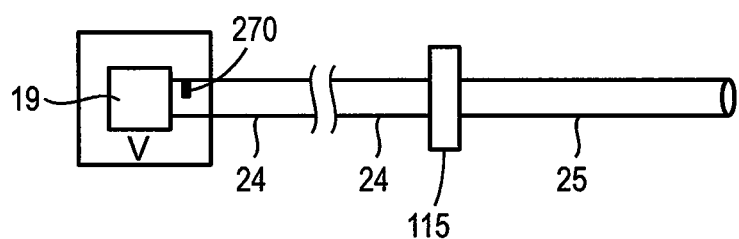

FIG. 38C shows an alternate location of strain gauges of the system described in FIG. 36 in which the gauge is located inside the ventilator.

DETAILED DESCRIPTION OF THE PREFERRED EMBODIMENTS

Figure 1:
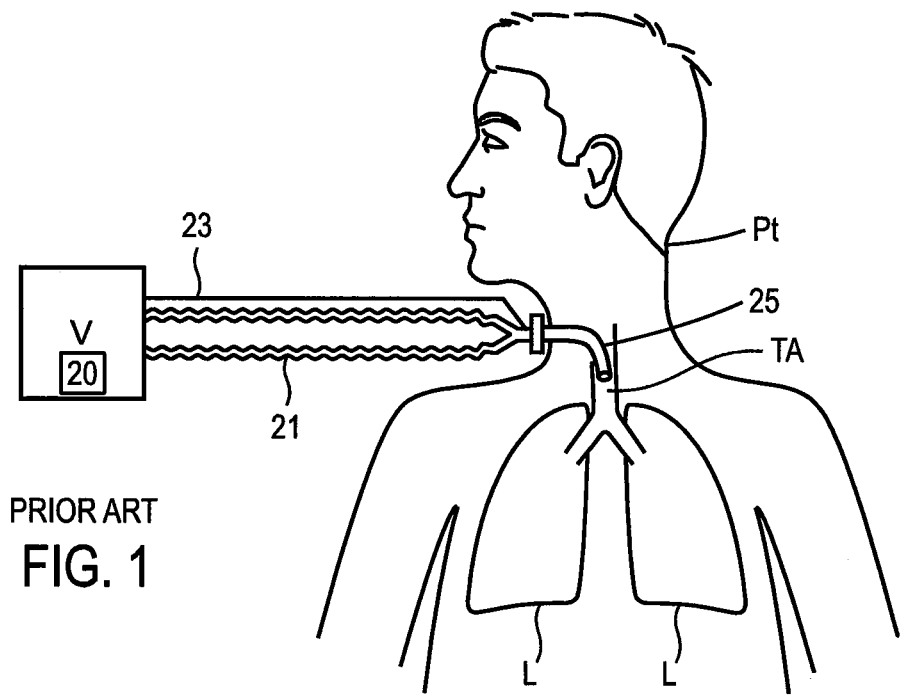
FIG. 1 shows prior art breath sensing in series with breathing circuit for ventilator control.
Figure 1A:
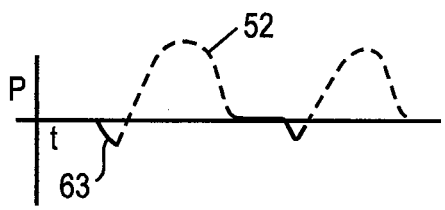
FIG. 1A shows graphical representation of the respiration signal masked by the ventilator gas delivery pressure.

FIG. 1 (prior art) describes a conventional ventilator system in which the breath sensor is in line with the ventilation gas being delivered in the breathing circuit. The Ventilator V delivers gas to the patient Pt through the ventilation gas delivery circuit, dual limb 21 and ventilation tube 25. A pressure tap 23 in series or in line with the ventilator gas flow senses a negative pressure created by a patient inspiratory effort. Alternatively, a flow sensor can be used in series with the ventilation circuit to detect when the patient inspires. The signal from the breath sensor is delivered to a ventilator control unit 20 in the ventilator V. As seen in FIG. 1a these in-series sensor systems measure the start of a patient inspiratory effort 63, but after the ventilator V is triggered to deliver a mechanical breath to the patient Pt, the sensor signal predominantly indicates the ventilator activity in the form of a ventilator gas delivery pressure tracing 52, and not the patient activity.

Figure 2:
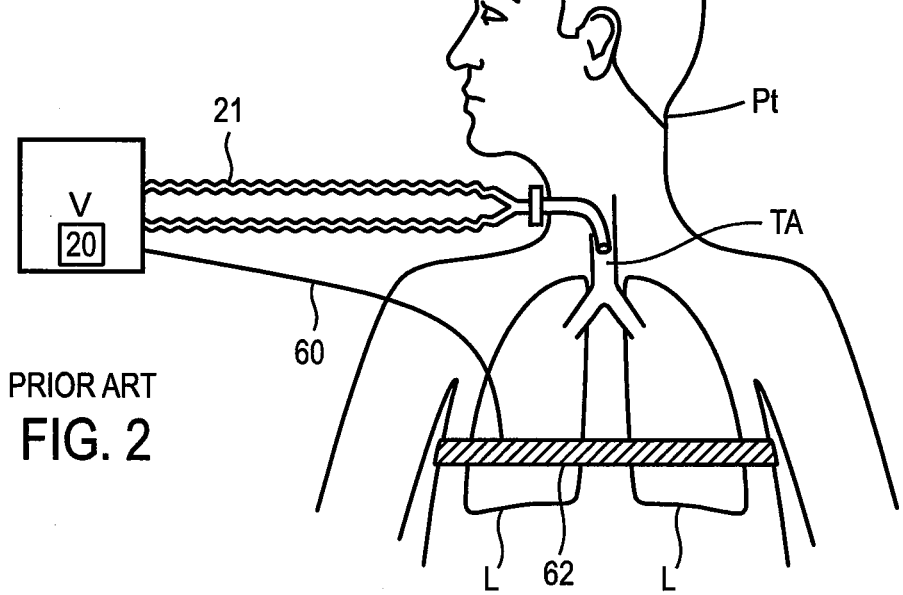
FIG. 2 shows breath sensing for ventilator control using chest impedance.
Figure 2A:
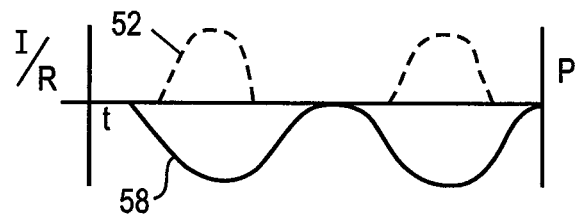
FIG. 2A shows a graphical representation of the ventilation gas delivery pressure and the respiration sensor signal.

FIG. 2 describes a ventilator breath sensing triggering system in which the breath sensor is a chest impedance sensor system, as described in U.S. Publication No. 2005/0034721. In this case, the sensor is placed in parallel with the ventilation circuit. A chest impedance band 62 is connected to the ventilator V control unit 20 by chest impedance wires 60. The patient spontaneous respiration curve 58 is not masked by the pressure waveform of the patient Pt, as shown in FIG. 2a. Although an improvement over prior art, the impedance sensor can have a tendency to register motion of the person which is not related to breathing and hence can include artifacts.

Figure 3:
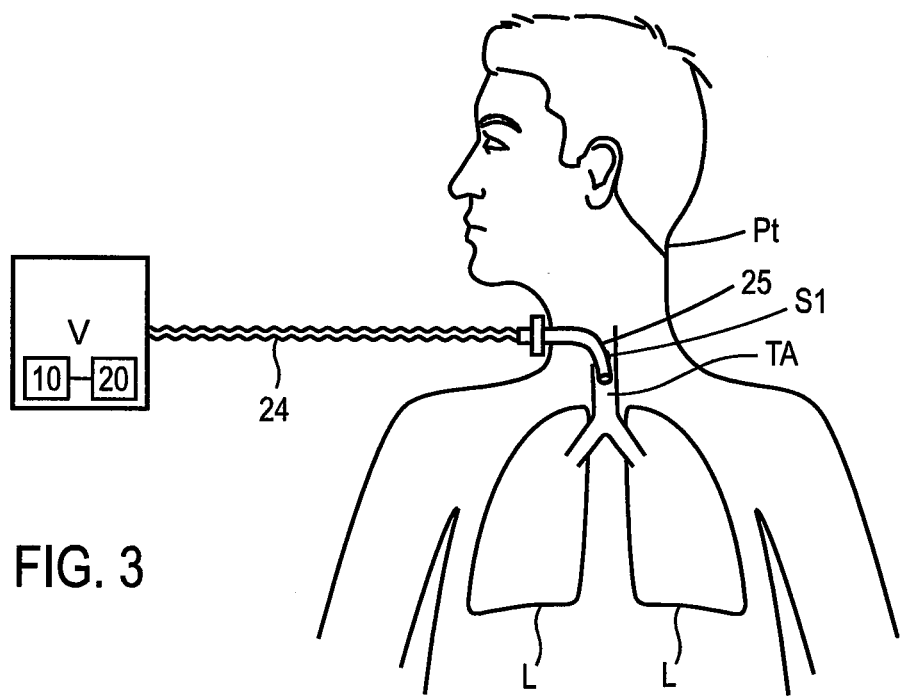
FIG. 3 shows an intra-airway breath sensing for ventilator control.
Figure 3A:
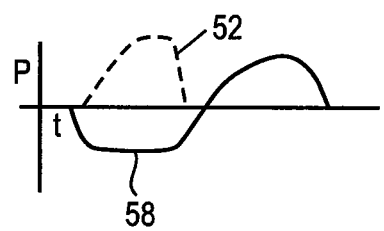
FIG. 3A shows graphical representation of the ventilation gas delivery pressure and the respiration sensor signal.

FIG. 3 describes an overall configuration of an embodiment of the present invention, including a ventilator V, a ventilation gas delivery circuit, single limb 24, ventilation tube 25 and sensor or pressure sensing port S1 positioned to measure intra-airway tracheal air flow or breathing pressures or nasal or oral air flow, positioned inside or near the airway. While the following exemplary embodiments are described for intra-airway tracheal air flow, similar concepts may apply to nasal and oral air flow. The breath sensor or sensing port S1 may be an intra-tracheal sensor, conduit or port located in the tracheal airway TA in the path of the patient's airflow, and in parallel with the ventilation circuit 24. The sensor, conduit or sensing port is typically but not always part of or attached to the ventilation tube 25. The signal may be delivered to the ventilator control unit 20 by means of wires or sensing conduits, or alternate transmission means such as fiber optic or wireless. The ventilator V may have one or more processors 10 for receiving and analyzing signals from the sensors. The processor 10 may process receive and process signals from the sensors and compute relevant parameters as described below. The processor 10 may then output the signals and/or the results of computations. The processor 10, ventilator V, and/or ventilator control unit 20 may then output the signals, the results of the analyzing and/or control ventilation based upon the analysis. As seen in FIG. 3a, this may be an improvement over conventional in-series breath sensing systems in that the actual breathing signal 58 is not masked by the ventilation gas delivery 52, and the sensor measures both the patient's true breathing activity 58 as well as the effect that the ventilation gas delivery has on the patient's lung pressure and airway breath flow. This is especially important in open ventilation systems. Also, as will be explained in later sections, the present invention describes improvements related to signal drift, artifacts, and disturbance caused by patient movement and changing temperature conditions. It should be noted that while in the following descriptions, the sensing system is described typically in conjunction with a transtracheal ventilation catheter, however this is exemplary only and other interfaces are included in the invention, such as but not limited to: a trans-nasal catheter, a trans-oral catheter, transtracheal tube catheters, percutaneous catheters, oral cannula, nasal cannula, non-invasive mask oral and/or nasal interfaces, open nasal and open oral cannula interfaces. For simplicity, the following describes are typically described with a transtracheal catheter; however, the invention is also applied to the other interfaces stated above.

Figure 4A:
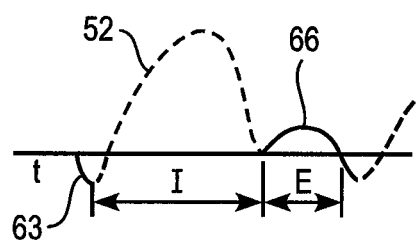
FIG. 4A shows graphically conventional breath sensing.
Figure 4B:
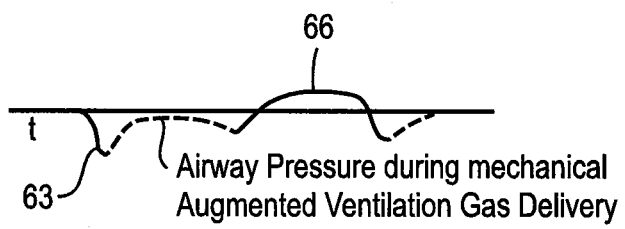
FIG. 4B shows graphically breath sensing described in this invention.
Figure 4C:
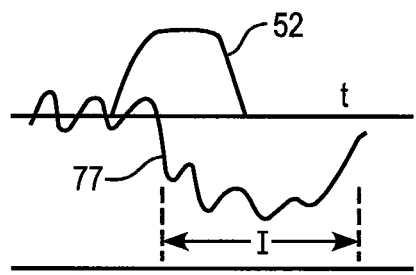
FIG. 4C shows graphically chest impedance breath sensing.

FIGS. 4a-4c graphically describes the difference between using intra-airway sensors which directly measure tracheal pressure and respiration, versus conventional in-line ventilator sensing systems. FIG. 4a describes a conventional system in which the pressure sensor measures a patient inspiratory effort 63 but then measures the ventilator gas flow 52. As one example of the disadvantages of this conventional system, the resultant inspiratory time determined by the ventilator is the inspiratory time set by the user on the ventilator, and not the true patient's spontaneous inspiratory time determined by a spontaneous breathing sensor, and for example as a result the patient's exhalation tracheal flow/pressure curve 66 begins later than the patient's true start of exhalation. FIG. 4b describes mechanical augmented ventilation in which tracheal pressure is measured at all times, hence during the period of ventilation gas delivery, the waveform accurately shows the combined effect in the lung or airway of spontaneous breathing and artificial ventilation. FIG. 4c shows a system with chest impedance sensors which show an artificial trigger of the ventilator gas delivery 52 due to an artifact in the chest impedance tracing 77 occurring before the true start of inspiration.

FIGS. 5-13 describe an embodiment of the invention in which intra-airway pressure may be measured using a combination of channels or conduits in the gas delivery circuit and/or the patient interface assembly, including for example in the gas delivery channel, in dedicated sensing conduits with sensing lumens or tubes, and in the annular space around the patient interface. The multiple channel sensing may provide the range, accuracy, resolution and reliability sought by the invention, as will be explained subsequently. The sensing system can be used with a transtracheal catheter interface, or other patient interfaces as described above, such as a nasal or oral catheter or cannula interface.

Figure 5:
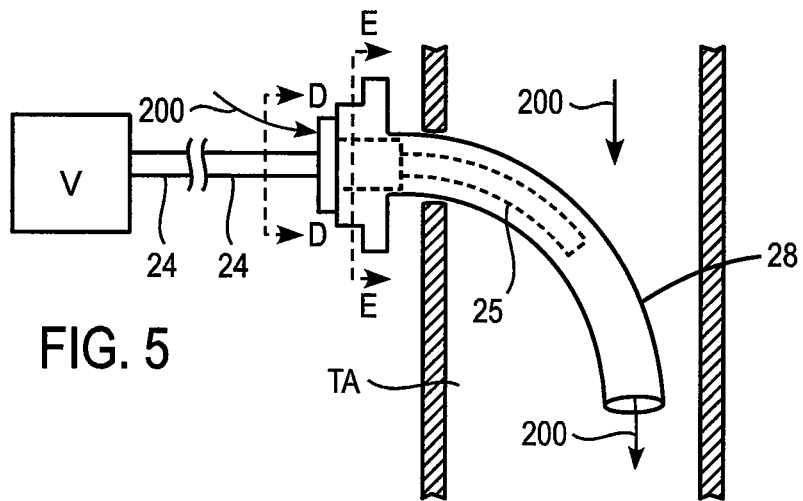
FIG. 5 shows a ventilation and breath sensing system in which a ventilation catheter is placed into a outer sleeve, such as a tracheostomy tube or stomal guide, with a heat moisture exchanger, bacterial filter, breathing port, spontaneous breath sensors, and an inspiratory valve positioned in the annular space between the catheter and outer sleeve.
Figure 5A:
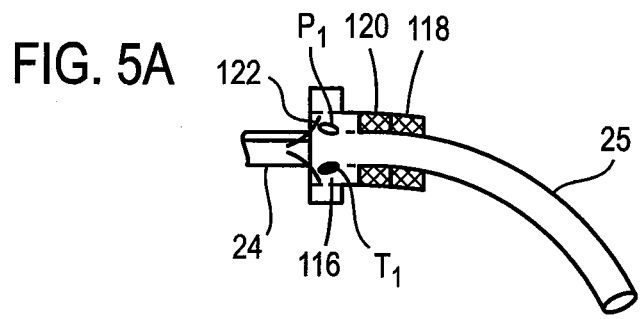
FIG. 5A shows the ventilation catheter of the system in FIG. 5.
Figure 5B:
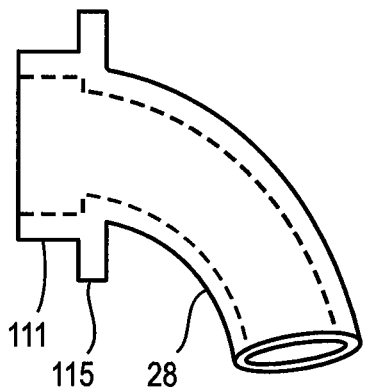
FIG. 5B shows the outer sleeve of the system of FIG. 5.
Figure 5C:
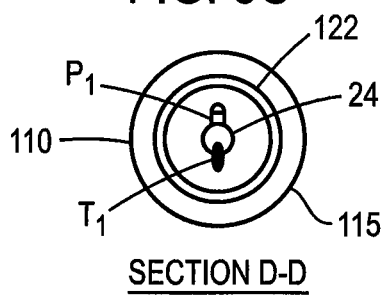
FIG. 5C shows the cross section through line D-D in FIG. 5.
Figure 5D:
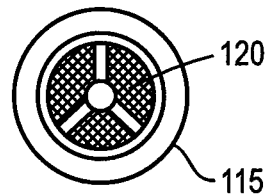
FIG. 5D shows the cross section through line E-E in FIG. 5.

FIGS. 5-5d describe an embodiment of the present invention in which a ventilation and breath sensing system may include a ventilator V, a gas delivery circuit 24, and a ventilation tube 25 or ventilation catheter placed into an outer sleeve, such as a tracheostomy tube 28 or a stomal sleeve (not shown). A ventilation catheter flange 115 may be provided and may be coupled to a tracheostomy tube ventilation circuit connector 111. FIG. 5a describes the ventilation tube 25; FIG. 5b shows the tracheostomy tube 28; and FIGS. 5c and 5d show the cross-section through lines D-D and E-E in FIG. 5, respectively. In addition to the patient inspiring spontaneously through the upper airway 200, optionally the patient can also inspire from ambient air through the annular space between the ventilation catheter and outer sleeve through an inspiratory flow valve 122 with a breathing flow port 116. This permits minimal work required to inspire ambient air, since air can be inhaled through the valve and also through the mouth and nose, while directing exhaled air through the upper airway to further facilitate speech. Optionally, a heat moisture exchanger 118 and a bacterial filter 120 can be provided in the annular space. Further, breath sensors can optionally be placed in the annular space, for example a thermal sensor T1 for detecting inspiratory and expiratory flow and/or a pressure sensor or sensing port P1 for measuring tracheal pressure. Optionally, an expiratory pressure relief valve can be provided so that if the patient airway pressure exceeds a safe limit, gas can be exhaled or vented through the relief valve (not shown). Optionally, a PEEP valve is provided (not shown) between the ventilation tube and tracheostomy tube, to maintain a level of pressure in the lung.

Figure 6:
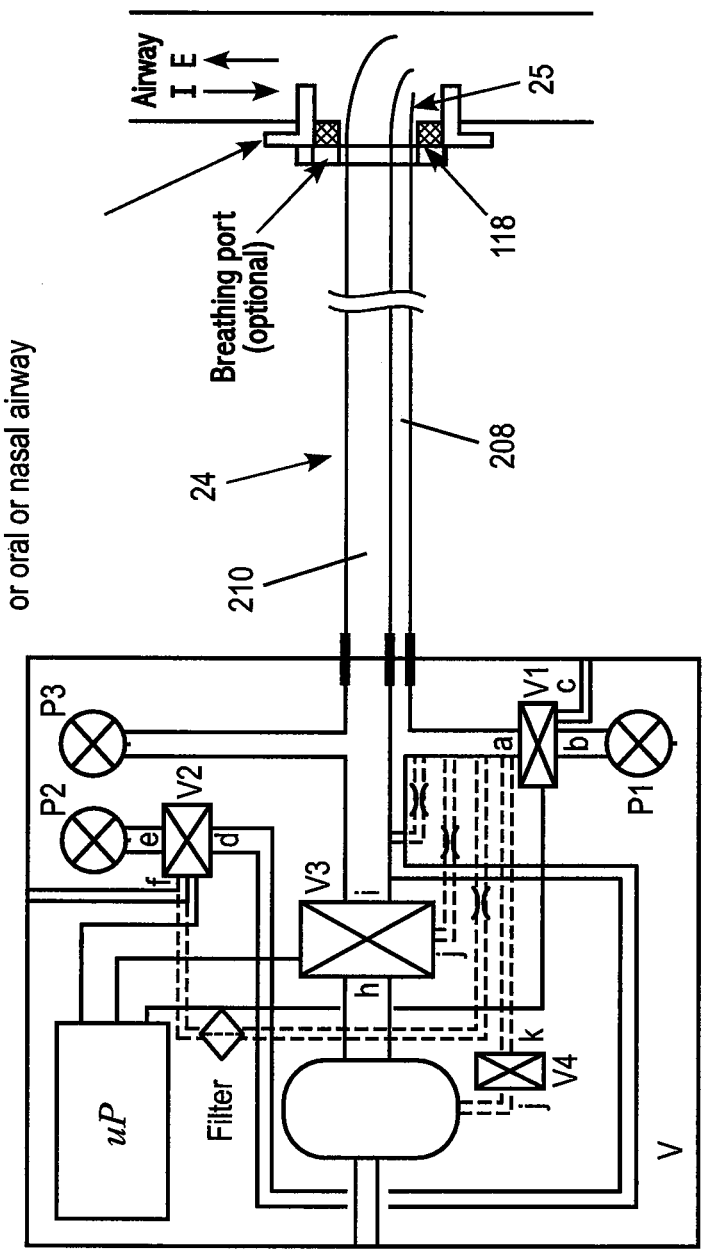
FIG. 6 shows a breath sensing and ventilation system in which an array of three pressure sensors are used to measure spontaneous breathing, intratracheal pressures, and ventilation gas delivery pressures.

FIGS. 6-9 describe an embodiment of the present invention with a ventilation breath sensing and control system using three pressure transducers to optimize the sensing of spontaneous breathing airway pressures and controlling and monitoring ventilator functions. FIG. 6 describes the overall layout and describes the purpose of the pressure transducers P1, P2 and P3. Transducer P1 has a range for example of −100 to +100 cmH2O with 0.1 cmH2O resolution. P1 is used for (1) airway alarm handling such as for high peak pressure and high inadvertent PEEP, (2) determination of respiratory rate, T(inspiration), T(expiration), end of expiration, end of inspiration, and start of expiration, and (3) airway pressure signal to be delivered to the GUI display screen for real time display of the airway pressure. P1 is open to the airway pressure sensing lumen continuously when the ventilator is powered on. It is decoupled from the sensing lumen when the ventilator power is off, through the closure of valve V1, in order to protect the valve from inadvertent misuse and overpressure conditions. Transducer P2 has a range for example of −20 to +20 cmH2O with a 0.025 cmH2O resolution. P2 is used expressly for the determination of the start of inspiration. The high resolution and accuracy near zero of the transducer maximizes the sensitivity of the system to detect the start of inspiration, which can be used for optimizing the response time of the system and synchronization of the ventilator output with the patients inspiratory phase. P2 is opened to the sensing lumen after the ventilator is powered on and after P1 determines the system is operating correctly without any inadvertent high pressure conditions. For example, P2 is opened to the sensing lumen after P1 determines that the breathing circuit and catheter are connected to the patient based on a normal breathing airway pressure signal detected by P1. During operation, P2 is cycled open and closed to the sensing lumen through valve V2. P2 is closed after the detection of inspiration, during the ventilator augmentation phase, in order to protect it from over-pressure damage that may occur from the ventilator pressure pulse. It is reopened to the sensing lumen upon completion of the ventilator augmentation phase. Optionally, P2 can be connected to the ventilation gas delivery channel rather than the sensing lumen, in order for P2 to provide a redundancy to P1. Or, optionally, an additional high resolution transducer similar to P2 can be attached to the ventilation gas delivery lumen for a redundancy to P1. Transducer P3 has a range for example of 0-30 psi. P3 is used for (1) monitoring of the ventilator augmentation waveform. (2) low gas delivery pressure, such as delivery circuit disconnect, or ventilator malfunction, low source gas pressure, and (3) high gas delivery pressure, such as delivery circuit obstruction, ventilator malfunction. P3 can also be used as a redundancy or cross check to P1 for measuring and monitoring airway pressure alarm handling functions, such as high PEEP and high peak airway pressure events and alarms, such as inadvertent PEEP and coughs or airway obstructions. P3 is open to the gas delivery circuit at all times. While FIG. 6 describes a transtracheal interface, the invention applies to other interfaces as described previously, such as oral and nasal catheter or cannula interfaces.

Figure 7:
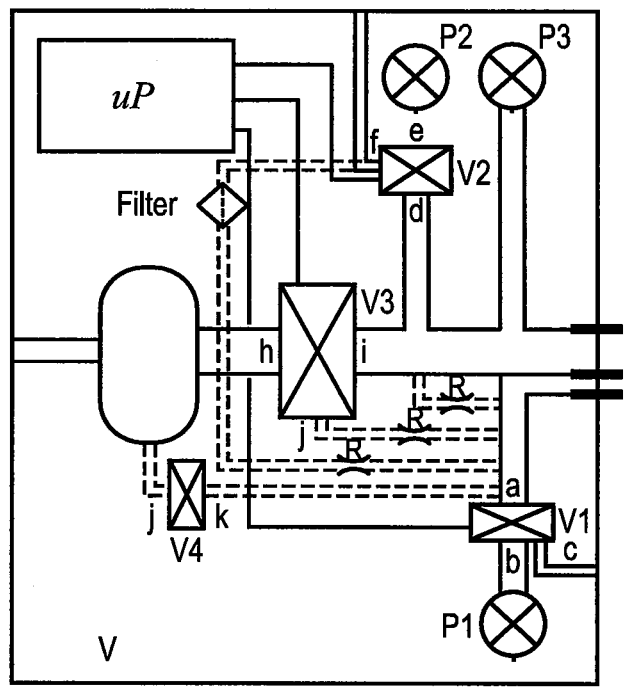
FIG. 7 shows a detailed view of the valving to operate the sensors of the system of FIG. 6.
Figure 8:
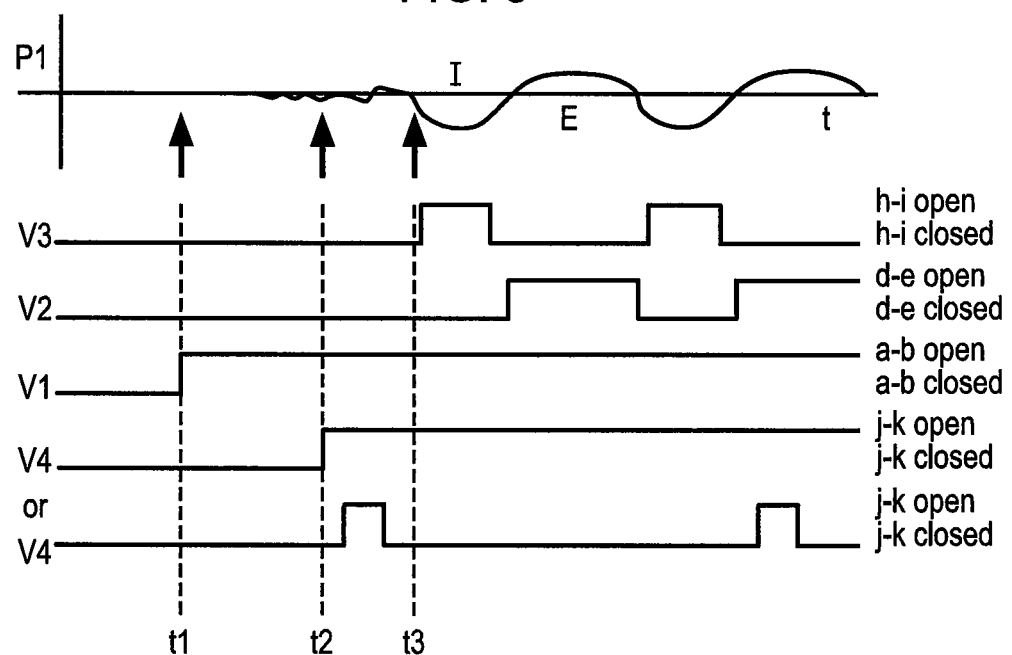
FIG. 8 shows valve timing control of the system described in FIG. 6.

FIG. 7 describes in more detail the valve control to control ventilator output and pressure transducer operation. Graph P1 in FIG. 8, with the timing diagrams, describes the airway pressure signal being generated by transducer P1. Signal V3 depicts the state of valve V3; when open the ventilator V is delivering pressurized augmentation gas to the gas delivery circuit. Signal V2 depicts the state of valve V2; when open P2 is in communication with the sensing lumen, or alternatively the gas delivery channel. Signal V1 depicts the state of the valve V1; when open, P1 is in communication with the airway pressure sensing lumen. Signal V4 depicts the state of valve V4 which controls a flow of purge gas through the sensing lumen to keep the sensing lumen patent, preventing moisture or secretions from blocking the P1 from detecting the airway pressure signal; when open, V4 allows the flow of purge gas through the sensing lumen, and can be opened continuously when the ventilator is powered on, or cyclically at a strategic cycle. The sequence of operation of the valves is as follows. Time t1 depicts the time of powering on of the ventilator, and the opening of valve V1 to the sensing lumen. Time t2 depicts the time of the gas delivery circuit being attached to the patient which is confirmed by a pressure signal starting to be detected by P1. Time t3 depicts the time that the breathing circuit and patient interface is attached correctly to the patient and the system is ready for normal operation.

Figure 9:
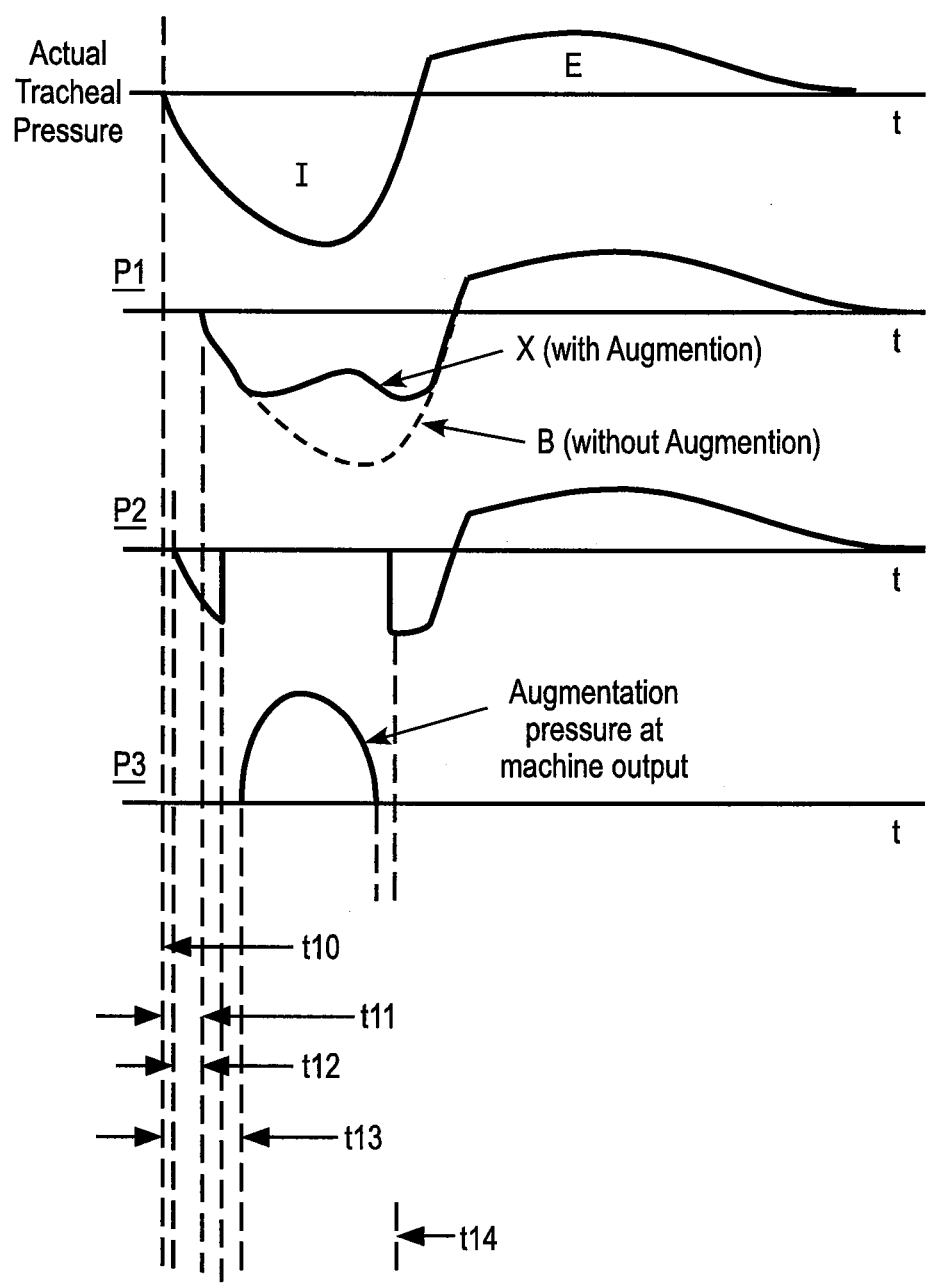
FIG. 9 shows resultant pressure tracings of the sensors used in the system of FIG. 6.

FIG. 9 describes in more detail the resultant pressure signals obtained by the pressure transducers, during one exemplary breath cycle. The top graph depicts actual tracheal or airway pressure, with an inspiratory phase I and an expiratory phase E. The second graph depicts the signal from sensor P1, indicating an increase in airway pressure compared to baseline B, corresponding in time with the augmentation pulse from the ventilator. The third graph depicts the signal from sensor P2, which measures the sensing lumen pressure, or alternatively the gas delivery circuit pressure. The valve V2 closes P2 to the sensing lumen when the ventilator augmentation output is on, depicted by the absence of a signal during the augmentation pulse. The forth graph depicts the signal from sensor P3 which measures the ventilator output augmentation pressure in the gas delivery channel. The time t10 depicts the actual start of inspiration based on actual change in tracheal airway pressure. Time t11 depicts the detection of the start of inspiration based on sensor P2, which can be for example a 5-30 msec response time delay from the actual start of inspiration, based on the time constant of the monitoring system. Time t12 depicts the time of closing off P2 from communicating with the sensing lumen by the closure of valve V2, which can be for example a 10-40 msec delay after the detection of the start of inspiration, based on the electromechanical response time of the system. Time t12 is typically 10-50 msec before the start of the augmentation delivery. Time t13 depicts the time that the ventilator augmentation gas flow begins, by opening valve V3, which is typically 50-150 msec after the actual start of inspiration, however can also include a deliberate delay so that the gas flow begins at a desired time within inspiration, such as when the patient's breathing effort reaches or is close to the maximum effort. Time t14 depicts the time after completion of ventilator augmentation gas flow at which time the P2 is reopened to be in communication with the sensing lumen. The delay between the end of augmentation gas delivery, and P2 obtaining the sensing lumen signal is typically 10-20 msec after the valve V3 turns off ventilator augmentation gas delivery.

Figure 10:
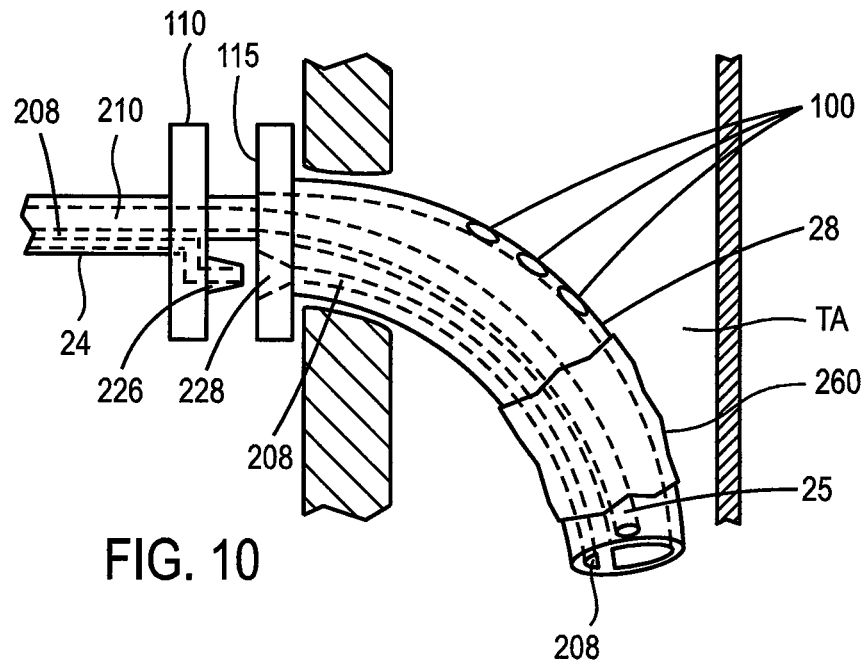
FIG. 10 shows a ventilation and breath sensing system comprising a ventilation catheter and outer sleeve such as a tracheostomy tube, with a sensing lumen in the outer sleeve, and with pneumatic coupling between the ventilation catheter and outer sleeve such that the ventilation catheter sensing lumen taps into the outer sleeve sensing lumen.

FIG. 10 describes an optional embodiment in which the ventilation tube 25 is placed inside an outer sleeve, such as a tracheostomy tube 28. A breathing pressure sensing conduit with a pressure sensing lumen 208 may be integrated into the tracheostomy tube 28. The tracheostomy tube connector 110 on the ventilation catheter 25 may include a sensing lumen connector 226 which engages with the tracheostomy tube sensing lumen 228 when the ventilation tube 25 is connected to the tracheostomy tube 28. The sensing lumen 208 may extend back to the machine end of the delivery circuit 24. A ventilator gas flow lumen 210 may pass through the ventilation gas delivery circuit 24. An optional low profile cuff 260 may be included. The tracheostomy tube 28 may include one or more outer cannula fenestrations 100.

Figure 11:
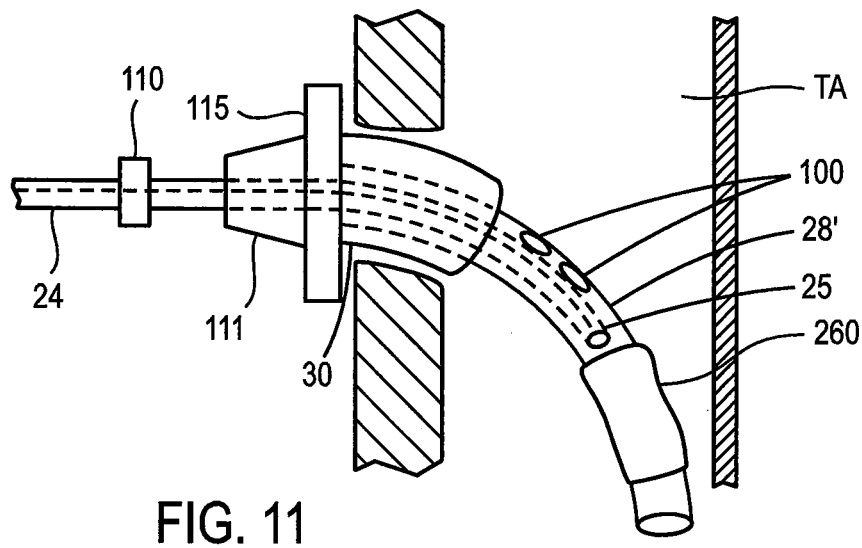
FIG. 11 shows a breath sensing and two piece ventilation interface in which a ventilation catheter is placed in a thin wall small diameter profile outer sleeve, such as a thin walled small diameter profile tracheostomy tube which includes a tight to shaft cuff when deflated and a stomal spacer, for the purpose of reducing resistance to upper airway breathing.

FIG. 11 describes an optional embodiment in which the ventilation tube 25 is placed into a thin wall small diameter tracheostomy tube 28'. The smaller profile of the tracheostomy tube 28' may minimize resistance to spontaneous breathing in the tracheal airway. Because of the smaller diameter, the tracheostomy tube 28' may include a stoma spacer 30, or optionally a tracheostomy tube outer cannula 28. The stoma spacer 30 can be reduced in size or can be replaced with different sizes in order to fit the stoma of the patient. A sensing lumen may be placed in the wall of the ventilation tube 25, or in the wall of the stoma spacer 30, or tracheostomy tube outer cannula 28', or optionally a sensing lumen can be a separate tube in the annular space around the outside of the ventilation tube 25. The tracheostomy tube 28' may include one or more outer cannula fenestrations 100. In FIGS. 10 and 11, the tip of the ventilation catheter is shown at different locations within the outer tube or tracheostomy tube, such as near the mid-point, or near the tip, or alternatively in the proximal half of the tracheostomy tube or alternatively beyond the distal tip of the tracheostomy tube.

Figure 12:
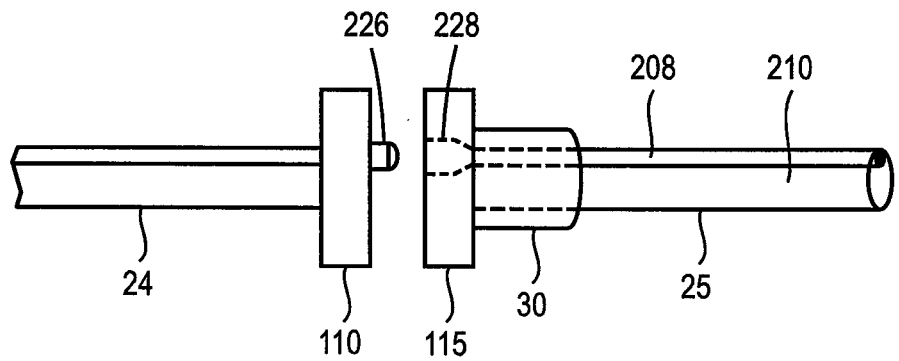
FIG. 12 shows two section breath sensing and ventilation delivery system in which an inserted disposable ventilation catheter section receives an external reusable gas delivery section, in which a sensor is positioned near the connector of the external section and connects to a sensing lumen of the inserted section.

FIG. 12 describes an optional embodiment with an external gas delivery circuit 24, which is external to the patient and connects to the ventilator V, and an internal ventilation tube section 25, which is placed so that the distal end is placed into the patient's airway. A sensing lumen 208 in the ventilation tube 25 may connect to a sensing lumen in the gas delivery circuit 24 when the two sections are connected through the pressure sensing lumen connectors 226 and 228. Optionally, a pressure transducer can be included in the connector 110 and can connect directly to the sensing lumen connection 228. This configuration may allow reuse of the external section and frequent cleaning and/or disposal of the internal section. Also, this configuration may allow for different models of the gas delivery section 25 to be used without removing the inserted section, for example, a long section gas delivery circuit can be attached when the patient is connected to a stationary ventilator, or during sleep, so that the circuit can reach the ventilator, and a short section gas delivery circuit can be attached when the person is wearing or toting the ventilator during mobile use of the system. Or when the patient pauses therapy, he or she can disconnect the gas delivery circuit without having to remove the inserted section, as might be important during certain activities.

Figure 13:
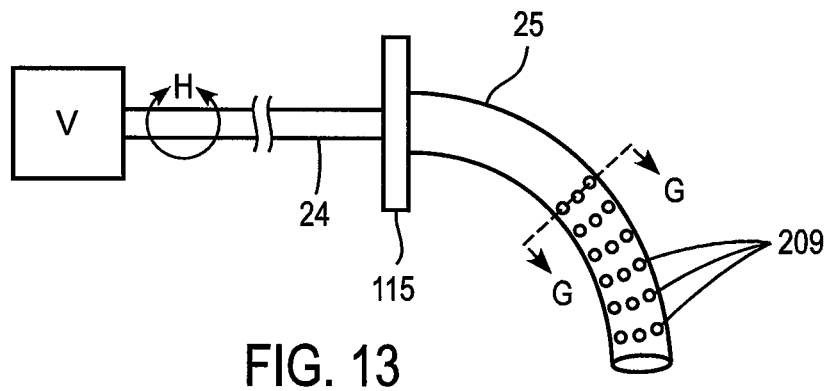
FIG. 13 shows a breath sensing and ventilation delivery cannula with an array of sensing lumens in the wall of the delivery cannula extrusion, and with a plurality of ports connecting the sensing lumens with the space outside the cannula, in order to provide multiple sites of pressure sensing in the airway.

FIG. 13 describes another main embodiment of the present invention in which the ventilation tube 25 includes a plurality of sensing lumens (not shown) in the construction of the ventilation tube 25. The multiple lumens may provide a plurality of sensing ports 209 on an inserted section of the ventilation tube 25, such that there are multiple opportunities to acquire a tracheal pressure signal. If one sensing port 209 clogs or rests against the tracheal wall tissue, or the inner wall of the tracheostomy tube or outer cannula or outer sleeve that surrounds the ventilation tube, there are still other sensing ports 209 available for sensing. For example, if a single port is used, and the port rests against the wall of the outer tube, such as a tracheostomy tube, outer cannula or stoma sleeve, then the port could be masked and have poor responsiveness to the airway pressure. The plurality of lumens can extend from the machine end of the gas delivery tube 24 to the distal end of the ventilation tube (as shown), or can extend for part of the distance (not shown). For example, the lumens can be terminated before reaching the distal tip of the ventilation tube, for example 1 mm to 20 mm from the tip. And for example, the lumens can be joined into a single lumen or few lumens in the gas delivery section so that fewer lumens extend between the ventilator and the ventilation tube.

Figure 13A:
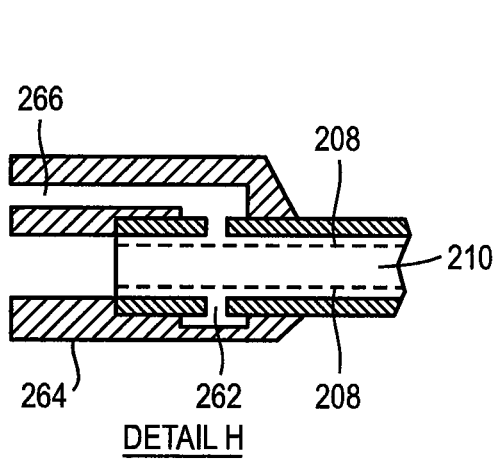
FIG. 13A shows a detailed view of a cross section through area H of FIG. 13.
Figure 13B:
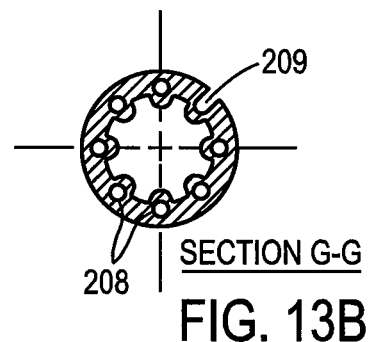
FIG. 13B shows a cross sectional view through line G-G of FIG. 13.
Figure 13C:
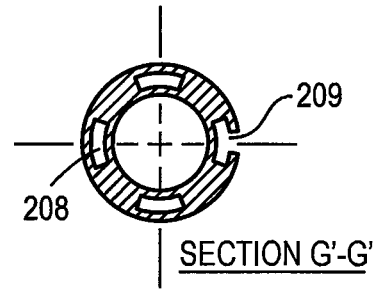
FIG. 13C shows a cross sectional view that is an alternative cross section to that of FIG. 13*b*.

FIG. 13a describes a detailed sectional view of the machine end of the delivery circuit at area H in FIG. 13 and describes the sensing lumen connector 266 of the sensing lumens 208 to the ventilator pressure sensing system, and the gas delivery connector 264 to the ventilator gas delivery system. Openings 262 may connect the sensing lumens 209 to the sensing lumen connector 266. FIG. 13b describes a sectional view of FIG. 13 at line G-G, describing the opening of a sensing lumen 208 to a sensing port 209. In this figure, ridges are described on the inner diameter of the ventilation tube; these provide space for the sensing lumens 208, but also serve to provide kink resistance of the ventilation tube. FIG. 13c describes an alternate configuration of sensing lumens 208 at the cross section at line G-G.

FIGS. 14-26 describe an embodiment of the invention in which intra-airway air flow measurements are made that correspond to the patient's spontaneous respiration pattern.

Direct measurement of airflow in the airway is a significantly useful technique in tracking the spontaneous breathing of the patient. Direct air flow measurements, for example, can be used to not only determine the inspiratory and expiratory phases, but also can determine strength of respiration or breathing effort. Air flow measurements can also be used to derive or estimate breathing volumes, to diagnose disease conditions such as breathing disorders, asthma or expiratory flow limitations, and to help distinguish between breaths and non-breath events. Pressure sensing elements may be separated by a distance and produce independent signals. Pressure differentials between pressure sensing elements determined from the independent signals may be used as input to determine pressure measurements. The pressure measurements may then be used to determine tracheal airflow. Tracheal airflow measurements may then be used to control ventilation.

Figure 14:
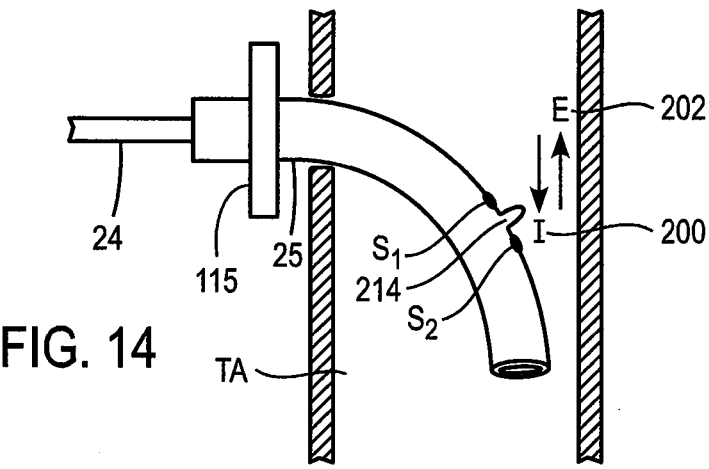
FIG. 14 shows breath sensing using two sensing elements with a physical screen between the elements to bias the response time of each element due to the direction of flow.
Figure 14A:
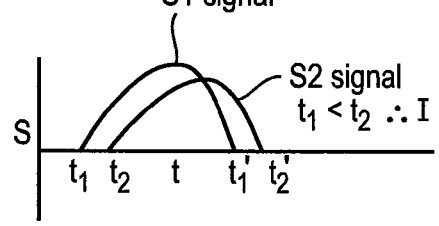
FIG. 14A shows graphically the signal tracings of the sensors shown in FIG. 14, during inspiration.
Figure 14B:
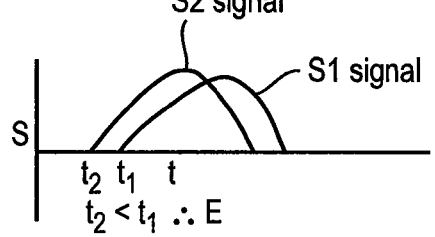
FIG. 14B shows graphically the signal tracings of the sensors shown in FIG. 14, during exhalation.
Figure 15:
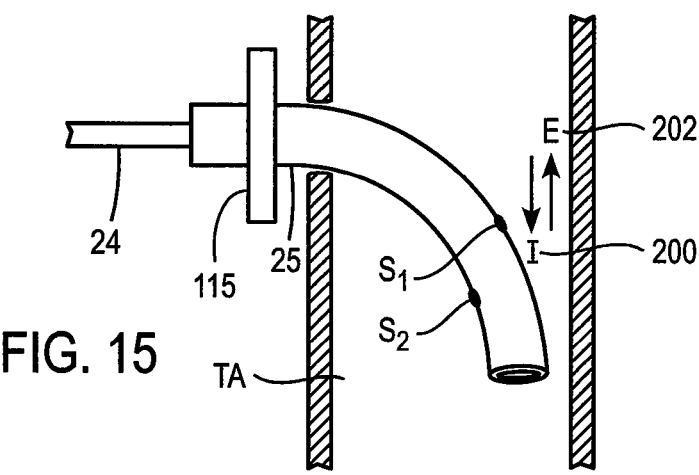
FIG. 15 shows breath sensing using two sensing elements on the inferior and superior aspects of the delivery cannula to create a physical barrier to bias the response time of each element that correlates to the direction of flow.
Figure 15A:
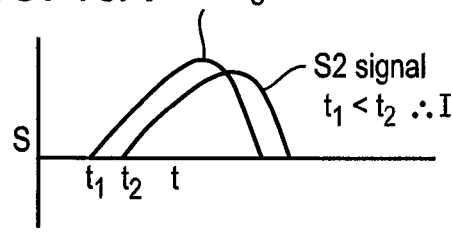
FIG. 15A shows graphically the signal tracings of the sensors shown in FIG. 15 during inspiration.
Figure 15B:
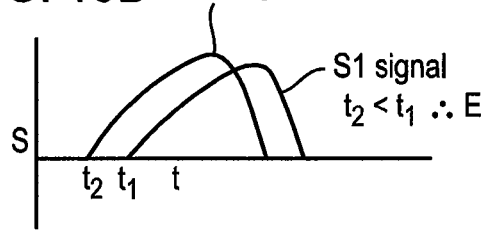
FIG. 15B shows graphically the signal tracings of the sensors shown in FIG. 15 during exhalation.

FIG. 14 describes an embodiment of the invention in which a ventilation tube 25 includes a physical screen or barrier 214 separating two sensing elements S1 and S2. The screen 214 provides a dampening or phase shift between the signals from the two sensors S1 and S2. As air flows in one direction, for example, inspiration, the signal strength of S1 is relatively strong and undampened, and the strength of S2 is relatively weak and dampened due to the dampening effect that the screen 214 has on airflow. Temporal and amplitude differences in the signal can be used to determine the direction of airflow. As shown in FIG. 14a, the S2 signal lags the S1 signal, and t1 is less than t2, hence the system knows the respiration phase is inspiration 200. As shown in FIG. 14b, the S1 signal lags the S2 signal, and t2 is less than t1 hence the system knows the respiration phase is exhalation 202. The sensing elements S1 and S2 can be pressure sensors or pressure sensing ports or may work on other principles such as temperature, sound, ultrasound, optical, or other. Alternatively to FIG. 14, FIG. 15 describes a ventilation tube in which the sensors or pressure sensing ports are separated by the ventilation tube 25 itself, achieving a similar result comparing the graphs shown in FIGS. 15a and 15b, with 14a and 14b.

Figure 16:
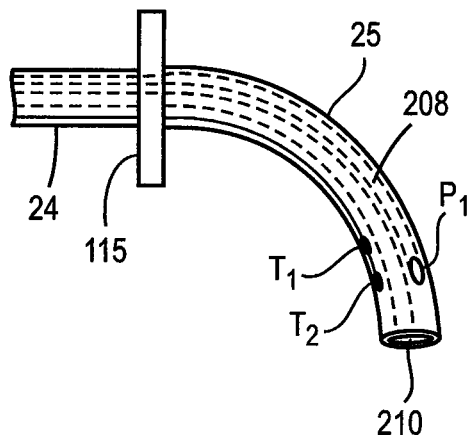
FIG. 16 shows breath sensing using two sensing systems, a thermal sensor for measuring tracheal airflow and a pressure sensor for measuring tracheal pressure.
Figure 16A:
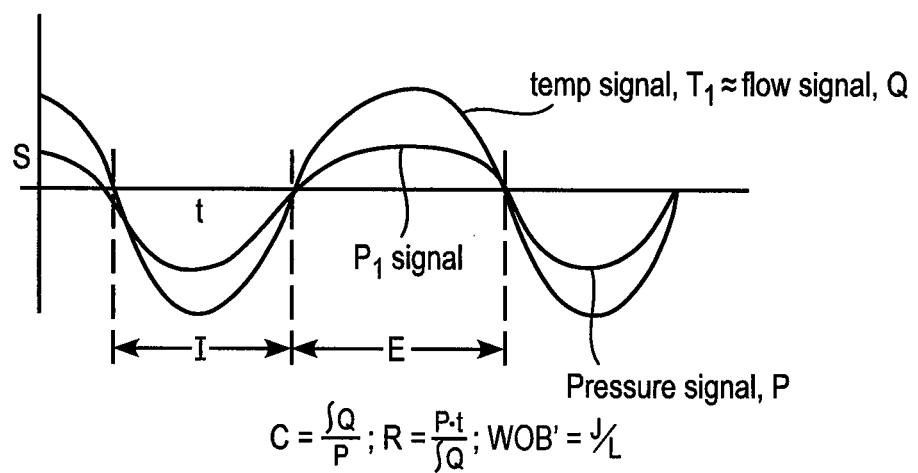
FIG. 16A shows resultant flow and pressure signals for system of FIG. 16, showing determination of compliance, resistance and an approximation for work of breathing.

In another embodiment of the invention, FIG. 16 describes a ventilation tube 25 that includes both a temperature sensing element T1 and a pressure sensor element or pressure sensing port P1 to obtain both a temperature-derived airway airflow signal and an airway pressure signal as shown in FIG. 16a. Optionally, a second temperature sensing element T2 can be used with T1 in a sensing array or Wheatstone bridge arrangement to compensate for drift and artifacts and to normalize the signal. The pressure signal can be used to determine breath phase as well as airway pressure (i.e., negative pressure may correspond to inspiration and positive pressure may correspond to exhalation), and the breath phase determination can be used to calibrate the temperature-flow signal to the correct phase of breathing, so inspiratory airway airflow can be distinguished reliably from expiratory airway airflow, regardless of the temperature conditions. The information obtained by this sensing configuration can be used to derive or estimate breathing volumes and breath effort, as well as determining the breath phases. Alternatively, the configuration can be used to determine lung compliance, airway resistance and an estimate of work of breathing, using pressure and flow, by establishing a correlation between airway pressure and pleural pressure, and a correlation between the flow signal and total flow. A flow signal, Q, multiplied by a correction factor or used in a differential equation governing the relationship between tracheal flow and other prevailing conditions, may provide a real time continuous estimate of total airway air flow rate, referred to as $Q'$. Compliance can be determined by the integral of $Q'$ divided by pressure measured by P1. Airway resistance can be determined by dividing the product of pressure of P1 and time by the integral of $Q'$. WOB can be estimated by multiplying the product of the integral of $Q'$ and pressure of P1 by a correction factor correlating P1 with pleural pressure. While in FIG. 16 the sensor is described as being inside an airway, the invention includes other placements of the sensors, for example, the pressure sensing port can be placed inside an airway, such as the tracheal, oral or nasal airway, while the thermal sensor can be placed in the proximity of the entrance to the airway, such as the tracheotomy or tracheostomy, oral or nasal airway. The thermal sensor proximity to the airway entrance can be slightly inside the opening to the airway, or directly at the entrance to the airway, or outside the entrance to the airway in the path of inspired and exhaled airflow.

FIG. 17 describes an embodiment of the invention in which a ventilation tube includes two sensing lumens, 208 and 208', which terminate along the inserted section of the ventilation tube 25 at different locations separated by a distance, at sensing ports Pp and Pd. The ventilation tube 25 can be inserted directly into the airway, or can be inserted into the lumen of an outer tube as described previously. A slightly different pressure signal may be applied to the two ports, labeled Pp and Pd in FIG. 18, during inspiratory flow and during expiratory flow. Therefore, a pressure differential, for example delta P during inspiration, can be measured. The measured delta P can be used in a flow rate equation to compute flow rate, while making the appropriate assumptions regarding the effective radius of the cross-sectional area of the trachea, the viscosity or density of the air in the trachea, and conditions form other effects such as drag. With this sensing configuration, both the tracheal pressure and tracheal airflow can be measured, monitored and used for display and ventilator control purposes. The flow information, and combination of flow and pressure information can be used as previously described. FIG. 17a describes an alternative configuration to FIG. 17 wherein the pressure ports are located on opposite aspects of the ventilation tube, an inferior surface for Pd and a superior surface for Pp.

FIG. 19 describes an alternate configuration in which the ventilation tube 25 is angulated, for example, approximating a right angle, and where the pressure sensing lumen pressure ports Pp and Pd are located on the distal straight section of the tube. This configuration creates spacing between the pressure ports that is parallel with the lumen of the trachea, aligning the pressure ports with the tracheal axis. FIG. 19a describes an alternative embodiment to the configuration in FIG. 19 in which the pressure ports Pp and Pd are on the proximal straight section of the ventilation tube, on the inferior and superior aspects.

FIG. 20 describes another main embodiment of the present invention in which the sensor S1 is flushed with flow exiting a flush port 220. FIG. 20a describes detail J of FIG. 20, illustrating a dedicated flush lumen 224, the flush port 220, and the sensor S1 of the ventilation tube 25. FIG. 21 describes an alternative embodiment to FIG. 20a wherein the flush lumen 224 branches off of the main gas delivery lumen 210. FIG. 22a describes an alternative embodiment in which the sensor S1 and the flush port 220 are located on the inferior/anterior side of the ventilation tube 25 as opposed to the superior/posterior side as previously illustrated. In addition, the sensor and flush port can be located on the lateral side, on the superior side, or on the inferior side of the ventilation tube (not shown). FIG. 22b describes an alternate configuration in which the flush port 220 flushes in the reverse direction back at the sensor S1. FIGS. 23a-c describe alternate pressure or flow delivery profiles of the flushing media being delivered, for example continuous shown in FIG. 23a, intermittent shown in FIG. 23c or as needed when the sensor signal appears degraded shown in FIG. 23b. The flushing media can also be delivered in a pulsatile waveform, or in any combination of the above. The flush media can be a respiratory gas such as oxygen, a therapeutic gas such as helium, humidified air, or a liquid such as saline or a medicant.

In FIGS. 24 and 26 another embodiment of the invention is described in which sensing elements or sensing ports are placed in a sensor flow conduit 206 in the tracheal airway TA. Inspiratory and expiratory flow may pass through the conduit 206. The conduit 206 may be positioned on the ventilation catheter such that the proximal and distal openings of the conduit 206 are in line with the axis of the tracheal airflow. The sensor signal can be correlated to airflow rate, based on for example known correlation factors and look up tables. For example, the sensors can be thermal sensors, and the slope of the sensor signal divided by the cross sectional area of the conduit may give a value in units of [(volts*[cross sectional area]^2)/time], which can be correlated to liters per minute based on a correlation factor of volts to distance. The resultant value is the flow rate Q(c) though the conduit. Q(c) can then be correlated to the flow rate in the trachea by a correlation factor correlating the conduit size with the tracheal lumen size. This sensor is useful in deriving the patient's spontaneous inspiratory and expiratory flow rates and breathing volumes as well as pressure.

Alternatively, two pressure sensors or pressure sensing ports can be included in the flow conduit, P1 and P2, and optionally as illustrated in FIG. 24a can be separated by a flow conduit screen 232 and positioned a distance apart to measure dynamic pressure drop across that distance and using Pouisille's Law. The pressure drop can be converted to flow rate, which can be integrated to obtain breathing volumes. Inspiratory flow 200 and expiratory flow (not shown) flows through the conduit and pressure is registered by the pressure taps P1 and P2. Tracheal pressure is also determined. Optionally a flush lumen and flush port (not shown) can be routed into the conduit 206 through a gas delivery tube and/or the ventilation tube 25 in order to maintain a patent flow conduit and screen, or optionally, flushing fluid can be delivered into the flow conduit through the pressure sensing lumens 208 leading to the pressure ports P1 and P2. Alternatively, the sensing flow conduit can be recessed on the outside wall of the ventilation tube, or flush with the outer profile of the ventilation tube, so that the outer surface of the tube does not protrude. Or alternatively, the sensing lumen can be within the ventilation tube, on the inside wall, or the sensing conduit can be the ventilation tube itself, with a proximal and distal entrance and exit port positioned in the airway. Or, alternatively, if the ventilation tube is used inside of an outer tube, as described previously, the sensing conduit can be part of the outer tube similar to the options described when associated with the ventilation catheter, or the conduit can be in the annular space between the outer tube and ventilation tube. As illustrated in FIG. 26a, the slope of the flow signal generated by the two sensors in the sensing conduit, can be divided by the trachea cross sectional area, and multiplied by a correction factor X to determine the total flow rate of the patient, from which effort, volume, and other breathing parameters can be derived.

FIG. 25 describes another embodiment of the invention in which a ventilation system includes a ventilator V, a gas delivery circuit 24 with a ventilator gas flow lumen 210, and a ventilation tube 25 placed in the patient's airway TA. A flow sensing lumen 208 is provided from the ventilator V to the patient's airway TA. The sensing lumen 208 can be open to atmosphere ATM at the proximal or machine end of the system so that when the patient breathes, a small portion of the inspiratory and expiratory flow moves through the sensing lumen 208. Pressure taps 219 and 221 are provided to measure pressure at different points of the sensing lumen 208 and registered on pressure sensors P1 and P2, respectively. In this manner tracheal pressure can be measured using pressure tap 219, which is proximal to the patient's airway, and a breathing flow rate can be derived by measuring the flow rate through the sensing lumen 208 calculating flow rate from the pressure drop across the pressure signals P2 and P1 shown graphically in FIG. 25b. The sensing lumen flow rate can be used to determine the relative strength or amplitude of tracheal airflow. FIG. 25a describes a cross sectional schematic of the system in FIG. 25. A ventilator gas delivery pump may be a compressor or accumulator. Optionally a flush media can be delivered to the sensing lumen flush lumen 224 to keep it free from obstructions as previously described.

FIGS. 27-32 describe an embodiment of the present invention in which a breath sensing transducer element is integrated into the patient interface, for example the ventilation tube 25 or the distal end of the ventilation gas delivery circuit 24 close to the patient, or the outer tube if used, such as a tracheostomy tube, a tracheostomy tube outer cannula, or a stoma sleeve or spacer.

FIG. 27 describes an embodiment of the invention in which a ventilation catheter 25 includes a micro pressure transducer 222 mounted on or near the stomal flange or catheter flange 115. The system may include a pressure sensing extension tube 218 extending from the flange 115 transtracheally into the airway of the patient and with a sensing port 216 on or near a distal end of the extension tube 218. This configuration may allow for a more sensitive and responsive measurement of tracheal breathing pressures compared to a conventional ventilator pressure-based breath sensor because of the transducer's proximity to the patient's airway. Also, during mechanical breaths delivered by the ventilator, the pressure measured by the transducer may be closer to lung or airway pressure rather than ventilator output pressure, again due to the proximity of the transducer to the patient. A wire may transmit the signal from the transducer back to the ventilator. Optionally, the signal can be transmitted wirelessly by a transmitter positioned somewhere near the flange or incorporated in the flange. For example, the transmitter can be placed in a neck band that is used to secure the flange and tube in place. This arrangement provides a minimum response time signal of tracheal pressure because the transducer is placed as proximal as possible to the airway without actually being placed in the airway. Placement of the transducer close to but not inside the airway may avoid at least some reliability and maintenance problems compared to configurations where the transducer is placed in the airway. FIG. 27a describes a cross section of an optional feature in which a flush lumen 224 is included in the gas delivery circuit 24. A flow rate of fluid is delivered from the ventilator through the flush lumen 224 to the extension tube sensing lumen 208 to keep the sensing lumen 208 free from obstructions or restrictions. The fluid can be a gas or a liquid as previously described. FIG. 27b describes a cross section of FIG. 27a showing in more detail the pressure transducer 222 sensing surface communicating with the sensing lumen 208, and the flush lumen connected 224 connected to the sensing lumen 208. While a pressure transducer is used in this example, other types of breath sensors can be used in the same arrangement, such as thermal sensors, for example, thermistors, strain gauge sensors, piezoelectric sensors, optical sensors, gas composition sensors or ultrasonic sensors.

FIG. 28 describes an embodiment of the invention in which a removably coupled two piece system is used, including an external reusable gas delivery section 24 and an internal disposable ventilation catheter section 25. The ventilation gas delivery channels 210 are interconnected with a pneumatic connector 230, shown in FIG. 28a. In addition to the advantages served by a removably coupled two piece system as described in FIG. 12, a two piece system may provide a cost advantage by including a relatively expensive transducer on the reusable external portion and not the disposable internal portion. As shown in the cross sectional schematic view in FIG. 28a, the reusable section may contain a micro pressure transducer 222 in the connector 110 or flange. When connected to the internal section connector 111, the pressure transducer pneumatic connector 226 may connect to a receptacle 228 to pneumatically communicate with a sensing lumen 208 in the inserted section. A flush lumen 224 can be provided in the external section, connected to a flush source in or near the ventilator V. The flush lumen 224 may connect with the sensing lumen 208 with a flush lumen connector 227 when the external and internal sections are joined. FIG. 28b describes an alternate configuration in which the sensing lumen 208 may be flushed with a flush lumen 224 branching off of the main gas delivery lumen 210, at one or multiple locations. While a pressure transducer is illustrated in this embodiment, the sensor can be of other sensing types as previously explained. The ventilation tube can be placed directly through a stoma into the airway of the patient, or in to an outer tube, as previously explained.

FIG. 29 describes an embodiment of the invention with a ventilation tube 25 inserted into an outer sleeve such as a tracheostomy tube 28. The ventilation tube 25 may include a micro pressure transducer integrated with the tube connector 110, and communicates with the ventilator V with a wire 92, or wirelessly as previously described. The transducer communicates through a connecting port 216 with a sensing lumen 208 of the ventilation tube 25. The ventilation tube sensing lumen 208 terminates at or near the tip of the ventilation tube 25, and may be recessed inside the tracheostomy tube 28, or may extend beyond the tracheostomy tube 28. The ventilation tube 25 can extend beyond the tracheostomy tube 28 as shown, or be recessed inside the tracheostomy tube 28, such as near the midpoint of the tracheostomy tube 28, or near the proximal end of the tracheostomy tube 28. Optionally, the sensing lumen 208 can terminate at the transducer, or can extend to the machine end of the system to be attached to a flushing source.

FIG. 30 describes an embodiment in which the sensing lumen 208 is part of a sensing tube 218 that extends for a short distance from the flange/connector 110. FIG. 30a describes a cross section of an optional embodiment of FIG. 30 in which a flush port 224 extends to the ventilator so that the sensing lumen 208 can be flushed to remain patent. The distal tip of the ventilation tube of FIGS. 30 and 30a can extend beyond the tracheostomy tube, can be flush with the tip of the tracheostomy tube, can be recessed inside the tracheostomy tube, or can be at the proximal end of the tracheostomy tube as previously described.

FIG. 31 describes an embodiment in which the ventilation tube 25 is inserted into a stomal sleeve or guide or stent 29 and includes a sensing tube 218 with a sensing lumen 208. In the various examples, optionally, the transducer 222 can be integrated into or attached to the tracheostomy tube, stomal sleeve or guide or stent, with a sensing lumen extending from the transducer into the airway. The sensing lumen can be a separate tube, can be inside of or outside of, or can be part of the tracheostomy tube, stomal sleeve or guide or stent. The ventilation tube can electrically attach to the transducer and optionally pneumatically connect with the sensing lumen to provide a flow for flushing to maintain its patency as previously described.

FIG. 32 describes an optional configuration in which a reusable pressure transducer 222 can be connected to the connector 110 of the gas delivery circuit 24 and connected to the sensing lumen connector 228 on the ventilation tube connector/flange 115. Thus, the pressure transducer assembly can be reusable while the remaining sections can be disposable. Optionally (not shown), the gas delivery circuit 24 and ventilation tube 25 can be a one piece assembly rather then two assemblies, and the pressure transducer assembly can attach to the one piece circuit and ventilation tube assembly. While the sensor illustrated in these examples is a pressure sensor, other sensors can be used as previously described.

Multiple options for configuring the micro pressure transducer 222, the gas delivery circuit 24 connection to the ventilation tube 25, and/or tracheostomy tube 28 can be employed. For example, the transducer 222 can be part of the gas delivery circuit, the ventilation tube 25, or the tracheostomy tube 28. Alternatively, the transducer 222 can be permanently attached, or removably attached. The gas delivery circuit 24 can be removably attached to the ventilation tube 25 or the tracheostomy tube 28. The sensing lumen 208 can be part of the ventilation tube 25 and/or tracheostomy tube 28, and can be a lumen in the construction of the tube(s) terminating at the tip of the tube, or terminating at a distance from the tip of the tube. Alternatively, the sensing lumen 208 can be a separate tube on the inside or outside of the ventilation tube 25 or tracheostomy tube 28. As previously mentioned the tracheostomy tube 28 can be a stoma sleeve or stent. The flush lumen can be a dedicated lumen from the gas delivery circuit 24 or can branch off of the gas delivery lumen at any location. The transducer can be integrated into a flange or a connector, or placed near the flange or connector for example in or on a neck collar. The transducer signal can be transmitted from the transducer to the ventilator control system with wires or wirelessly as well, for example by placing a transmitter in the neck band of the patient, or in a module that can be placed inside the persons shirt for example.

FIGS. 33 to 38 describe an embodiment of the invention in which other types of breath sensing transducers and sensing elements are used. The types of transducers and elements are used in arrangements that improve reliability, response time and accuracy.

FIG. 33 describes another embodiment of the present invention in which a fiber optic pressure sensor 240 may be placed on the ventilation tube 25, and the signal may be transmitted to the ventilator V through wires or fiber optic fibers 242. FIG. 33a describes an optional configuration in which the fiber optic sensor 240 is located on the outside surface of the ventilation tube 25, and optionally is recessed from the tip of the ventilation tube. FIG. 33b describes an alternative configuration in which the fiber optic sensor 240 is located on the inside of the ventilation tube 25 recessed from the tip.

FIG. 34 describes an optional embodiment in which the ventilation tube includes a fluid filled sensing lumen 244, and a micro pressure transducer 222 in or near the connector 110 or flange 115 of the gas delivery circuit 24. The micro pressure transducer 222 may sense pressure in the sensing lumen 244 and transmits the signal to the ventilator V.

FIG. 35 describes an optional embodiment in which the fluid filled sensing lumen 244 extends for a longer distance toward the ventilator V, or the entire distance to the ventilator V. FIG. 35a describes an optional embodiment in which the sensing lumen 244 terminates at a point recessed from the tip of the ventilation tube 25.

FIGS. 36-38 describe another embodiment of the present invention in which strain gauge sensors 270 are used to sense tracheal airflow and tracheal pressure. The resistance or voltage signal of the strain gauge element may be measured to determine the deflection level of the element. The elements are preferably placed in a recessed area of the ventilation tube 25 so that the elements are protected from resting against the tracheal wall. FIG. 36a describes the stain gauge element being protected by a shield 136 by being recessed. Either two elements can be used, and placed in a circuit configuration such as a wheatstone bridge to compensate for drift and artifacts, or a single element can be used. FIGS. 36b-f describe alternate ventilation tube positions for placing the strain gauge elements 270, including on the inferior/anterior aspect of the ventilation tube 25 (as shown in FIG. 36b), on the sides of the ventilation tube 25 (as shown in FIG. 36c), multiple locations around the tube 25 (as shown in FIG. 36d and FIG. 36e), and inside the ventilation tube 25 in a sensing lumen 208 (as shown in FIG. 36f).

FIG. 37 describes the resultant signal from the strain gauge 270. FIGS. 37a, 37b, 37c and 37d show corresponding deflection of the strain gauge 270 for different portions of the breathing curve represented by t1, t2, t3 and t4, respectively.

FIGS. 38a-c illustrate different locations for the stain gauge 270 throughout the ventilation gas delivery system, in which case the stain gauge 270 may be used to measure spontaneous breathing effort by the patient but also the ventilation gas delivery flow or pressure. In FIG. 38a, the strain gauge 270 is located in a tracheostomy tube connector 110. In FIG. 38b, the strain gauge 270 is located in the ventilation gas delivery circuit. In FIG. 38c, the strain gauge 270 is located in the ventilator V.

The embodiments described above are exemplary and certain features can be combined in all reasonable combinations. The sensors or sensing ports can be disposed on the ventilation catheter or ventilation tube or on an outer sleeve, and can be placed on the anterior, posterior, inferior, superior or lateral sides, or combinations thereof. The ventilation catheter or tube can be inserted directly into a stoma, or into a tracheal sleeve, such as a tracheostomy tube, stoma guide or stent. The ventilation catheter or tube and the sleeve, if used, can be comprised of a variety of shapes and curves, and can include protective features to protect the sensors and centering features to center the catheter or tube in the airway. In the case that the ventilation catheter or tube is placed directly in through the stoma, shapes and protective features may be employed to prevent the sensing element from contacting the tracheal wall and signal disruption. In the case that the ventilation catheter or tube is placed into a sleeve such as a tracheostomy tube, the sensors can be inside the tracheostomy tube for protection. Typically the tracheostomy tube is fenestrated so that there is adequate airflow past the sensors during inspiration and exhalation.

In addition, while the embodiments have been described as transtracheal or with a transtracheal ventilation tube or interface, they can also be endotracheal, oral, nasal, or face or nose mask interfaces. For example, the patient interface can be a trans-nasal or trans-oral catheter entering the airway from the nose or mouth. Or, the patient interface can be a open oral or open nasal cannula or catheter, in which the distal end of the cannula or catheter can be adapted to be positioned slightly inside the oral or nasal cavity, or at the entrance to the oral or nasal airway, or outside of the oral or nasal airway directed at the entrance to the airway. Or, the patient interface can be an oral and/or nasal mask. In the case of the more invasive interfaces or catheters, the tip of the catheter can be located in any of the lung airways. In the case of the less invasive interfaces, the tip of the catheter can penetrate the airway barely. In the case of non-invasive interfaces, the tip of the tube, cannula, or mask can be outside of the airway.

The ventilation tube or tracheostomy tube may include an inflatable and deflatable cuff, and the sensors or sensing lumens can be provided on the distal and proximal side of the cuff (not shown) to sense pressures or flows on both sides of the cuff, to provide an indication of the resistance being caused by the cuff. For example if the cuff is not completely deflated, the data from the two sensors or sensing ports may register a higher than expected pressure drop, indicating to the user that the cuff is not fully deflated for upper airway breathing, or the tube is too big for that particular patient or situation. Optionally the two sensors can be used to monitor cuff inflation if and when closed ventilation is being applied to the patient.

The pressure sensing elements described are typically diaphragm or bellows type elements. The pressure sensing elements, however, can be polymers, or other piezoelectric, optical, ultrasonic elements.

The ventilation therapy described herein can be augmented ventilation in which the patient is receiving a portion of their tidal volume from the ventilator, can be open ventilation in which the patient is spontaneously breathing through their upper airway, or can be closed or partially closed ventilation in which the patient's effort triggers the ventilator. The delivery circuit can be a single limb breathing circuit or dual limb breathing circuit. The invention can be applied to respiratory insufficiencies such as COPD, forms of neuromuscular weakness and paralysis, or airway disorders such as sleep apnea therapy. The therapy can be applied to adults, pediatrics and neonates.

The information made available by the breath sensors described herein can be used to synchronize ventilator functions to the patient's breath cycle, but can also be used to automatically adjust ventilator output and can be used for diagnostic purposes and trending analysis. The ventilator functions being controlled by the sensor information can be (1) delivery timing of gas from the ventilator, for example at a certain point of the inspiratory phase, a certain point of the expiratory phase, etc.; (2) amplitude, speed or waveform shape of ventilator output; or (3) frequency of ventilator output; or (4) composition of ventilator output, or combinations of the above.

Typical dimensions of the embodiments, assuming a transtracheal catheter interface are listed below. Dimensions for other interfaces, such as oral or nasal catheters or cannula may include the requisite dimensional adjustments.

1. Ventilation tube or catheter: 2 mm OD to 12 mm OD, preferably 3-5 mm, 0.5-6 mm ID, preferably 1-3 mm ID. Insertion length 10 mm to 150 mm, preferably 30-100 mm. Curved such that there is a distal straight section aligned with the lumen of the trachea. Durometer 40-80 Shore D.

2. Single limb ventilation circuit: 4 mm OD to 12 mm OD, preferably 5-8 mm OD, and 24-48 inches in length.

3. Outer Sleeve (tracheostomy tube): 4-10 mm ID, preferably 5-8 mm ID, with 1-2 mm wall thickness.

4. Outer Sleeve (thin wall minimal profile tracheostomy tube): 4-8 mm ID, preferably 5.5-6.5 mm ID with 0.75-1.25 mm wall thickness. 40 mm-120 mm length, preferably 60-90 mm.

5. Outer Sleeve (stoma guide): 4-10 mm ID, preferably 5-8 mm ID, with 1-2 mm wall thickness. 20-50 mm length, preferably 25-35 mm length.

6. Gas delivery lumen: 0.5-6 mm ID, preferably 1-3 mm ID.

7. Sensing lumen: 0.25-3 mm ID, preferably 0.5-1.75 mm and most preferably 0.75-1.5 mm.

8. Micro Pressure transducer: 1 mm-8 mm length and width dimensions, 1-5 mm thickness.

9. Fiber optic pressure transducer: 0.5-3 mm cross sectional dimension at the sensing element, preferably 1-2 mm.

10. Flow conduit: 0.5-2.0 mm ID, preferably 1-1.5 mm ID.

11. Flush port: 0.25-2 mm width or length or diameter.

12. Flush lumen: 0.2 mm-1.0 mm, preferably 0.25-0.5 mm.

LIST OF REFERENCE SYMBOLS

| | |
|---|---|
| Atm: | atmosphere |
| B: | Baseline |
| E: | Expiratory |
| I: | Inspiratory |
| L: | Lung(s) |
| P1, P2, P3: | pressure transducer 1, 2 and 3 |
| Pp: | proximal pressure sensor port |
| Pd: | distal pressure sensor port |
| Pt: | Patient |
| Pf: | Flush pressure level |
| Q: | Tracheal airflow trace |
| Q': | Estimate of total airway air flow rate |
| S1, S2, S3: | sensing elements |
| TA: | Tracheal airway |
| T, t1, t2, t3: | time |
| T1: | thermal sensing element one |
| T2: | thermal sensing element two |
| V: | Ventilator |
| V1, V2, V3, V4: | valves 1, 2, 3 and 4 |
| WOB: | Work of breathing |
| WOB': | Work of breathing |
| X: | Constant |
| 10: | Processor |
| 20: | Ventilator control unit |
| 21: | Ventilation gas delivery circuit, dual limb |
| 23: | Pressure tap |
| 24: | Ventilation gas delivery circuit, single limb |
| 25: | Ventilation tube |
| 28: | tracheostomy tube outer cannula |
| 28': | Thin wall small diameter tracheostomy tube |
| 29: | Stoma Sleeve |
| 30: | Stoma spacer |
| 52: | Ventilator gas delivery pressure tracing |
| 58: | Patient spontaneous respiration curve |
| 60: | Chest impedance wires |
| 62: | Chest impedance band |
| 63: | Patient inspiratory effort |
| 66: | Patient exhalation tracheal flow/pressure curve |
| 77: | Chest impedance tracing |
| 92: | Breath sensor wiring |
| 100: | Outer cannula fenestration(s) |
| 110: | Ventilation Catheter to tracheostomy tube connector |
| 111: | tracheostomy tube ventilation circuit connector |
| 115: | Ventilation catheter flange |
| 116: | Ventilation catheter - outer cannula breathing flow port |
| 118: | Ventilation catheter - outer cannula heat moisture exchange |
| 120: | Ventilation catheter - outer cannula filter |
| 122: | Inspiratory valve |
| 136: | Sensor protective shield |
| 200: | Inspiratory flow |
| 202: | Expiratory flow |
| 206: | Sensor flow conduit |
| 208: | Sensing lumen |
| 208': | Sensing lumen |
| 209: | Sensing ports |
| 210: | Ventilator gas flow lumen |
| 214: | Sensor physical barrier |
| 216: | Pressure sensor sensing port |
| 218: | Pressure sensing extension tube |
| 219: | Sensing lumen pressure tap, proximal |

-continued

| | |
|---|---|
| 220: | Sensor flush port |
| 221: | Sensing lumen pressure tap, machine end |
| 222: | Micro transducer |
| 224: | Flush lumen |
| 226: | Pressure sensing lumen connector, male |
| 227: | Flush lumen connector |
| 228: | Pressure sensing lumen connector, female |
| 230: | Gas delivery lumen connector |
| 232: | Flow conduit screen |
| 240: | Fiber optic pressure transducer |
| 242: | Fiber optic signal conduction fibers/wires |
| 244: | Fluid filled sensing lumen |
| 260: | Low profile cuff |
| 262: | Opening |
| 264: | Gas delivery connector |
| 266: | Sensing lumen connector |
| 270: | Strain gauge sensor |

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A ventilation and breath sensing apparatus comprising:
a ventilation gas delivery circuit;
a ventilation tube coupled to the ventilation gas delivery circuit and further defined by a patient airway end;
a plurality of pressure sensing elements disposed on the patient airway end of the ventilation tube and separated by a distance, each producing independent signals, airflow through a patient airway being derived from direct measurements of pressure differentials between the plurality of pressure sensing elements;
wherein control over at least one of ventilation gas delivery timing, amplitude, speed, waveform shape, frequency, and composition is based upon a correlated combination of the signals from the pressure sensing elements and the derived airflow to adapt to a true breathing activity by a patient.

2. The ventilation and breath sensing apparatus of claim 1, wherein the plurality of pressure sensing elements are pressure sensing conduits.

3. The ventilation and breath sensing apparatus of claim 1, wherein the plurality of pressure sensing elements are pressure sensing transducers.

4. The ventilation and breath sensing apparatus of claim 1, wherein the plurality of pressure sensing elements are a combination of pressure sensing conduits and pressure sensing transducers.

5. The ventilation and breath sensing apparatus of claim 1, wherein at least one of the plurality of pressure sensing elements is associated with the ventilation tube.

6. The ventilation and breath sensing apparatus of claim 1, wherein at least one of the plurality of pressure sensing elements is associated with the ventilation gas delivery circuit.

7. The ventilation and breath sensing apparatus of claim 1, wherein at least one of the plurality of pressure sensing elements is associated with a ventilator.

8. The ventilation and breath sensing apparatus of claim 1, wherein at least one of the plurality of pressure sensing elements is a pressure sensing conduit, and the pressure sensing conduit has at least one port.

9. The ventilation and breath sensing apparatus of claim 1, wherein at least one of the plurality of pressure sensing elements is a transtracheal sensing conduit, and wherein at least one of the plurality of pressure sensing elements is coupled to the ventilation gas delivery circuit.

10. The ventilation and breath sensing apparatus of claim 1, wherein two or more of the plurality of pressure sensing elements are at a distal end of the ventilation tube for positioning in at least one of a tracheal, nasal and oral airway.

11. The ventilation and breath sensing apparatus of claim 1, wherein the ventilation tube is removably coupled to the ventilation gas delivery circuit.

12. The ventilation and breath sensing apparatus of claim 1, wherein the ventilation gas delivery circuit includes a first pressure sensing element and the ventilation tube includes a second pressure sensing element, and wherein in a coupled arrangement, the first pressure sensing element and the second pressure sensing element are in fluid communication.

13. The ventilation and breath sensing apparatus of claim 1, further comprising a tracheal, nasal or oral airflow conduit coupled to a distal end of the ventilation tube that is for positioning within a tracheal, nasal or oral airway, wherein the plurality of pressure sensing elements are disposed within the tracheal, nasal or oral airflow conduit.

14. The ventilation and breath sensing apparatus of claim 1, further comprising a spontaneous breathing conduit separate from the ventilator gas delivery circuit for extending into at least one of a tracheal, nasal and oral airway, wherein the spontaneous breathing conduit comprises a plurality of pressure taps for measuring pressure drop across the plurality of pressure taps.

15. The ventilation and breath sensing apparatus of claim 1, further comprising an outer sleeve, wherein the ventilation tube is disposed in the outer sleeve.

16. The ventilation and breath sensing apparatus of claim 1, wherein the ventilation tube includes a patient interface.

17. The ventilation and breath sensing apparatus of claim 16, wherein at least one of the plurality of breath sensing elements is located in the patient interface.

18. The ventilation and breath sensing apparatus of claim 1, further comprising a physical barrier between at least two of the plurality of pressure sensing elements.

19. The ventilation and breath sensing apparatus of claim 18, wherein the physical barrier creates a pressure drop and biases the response time of each of the at least two of the plurality of pressure sensing elements depending on direction of airflow.

20. The ventilation and breath sensing apparatus of claim 1, further comprising at least one thermal sensor disposed near or in an entrance of an airway, wherein the at least one thermal sensor is used to determine spontaneous breathing airflow, and at least one of the plurality of pressure sensing elements is used to determine breathing pressure, and wherein a combination of the spontaneous breathing airflow and the breathing pressure is used to optimize ventilator synchronization and titration of therapy.

21. A ventilation and breath sensing method comprising:
  directly measuring airway pressure from a first pressure sensing element;
  directly measuring airway pressure from a second pressure sensing element, wherein the second pressure sensing element is separated by a distance from the first pressure sensing element, and the first pressure sensing element produces a first signal independent from a second signal from the second pressure sensing element;
  determining a pressure differential between the first signal and the second signal;
  determining at least one of a tracheal, nasal and oral pressure based upon the pressure differential between the first signal and the second signal;
  determining at least one of a tracheal, nasal and oral airflow representative of a true breathing activity of the patient using the corresponding one of the tracheal, nasal and oral pressure;
  initiating ventilation from a ventilator based upon a combination of at least one of the determined tracheal, nasal and oral airflow and at least one of the tracheal, nasal, and oral pressure.

22. The ventilation and breath sensing method of claim 21, wherein the plurality of pressure sensing elements are pressure sensing conduits.

23. The ventilation and breath sensing method of claim 21, wherein the plurality of pressure sensing elements are located within at least one of a tracheal, nasal and oral airway.

24. The ventilation and breath sensing method of claim 21, wherein the plurality of pressure sensing elements are located within an interface between the ventilation tube and the ventilation gas delivery circuit.

25. The ventilation and breath sensing method of claim 21, further comprising determining spontaneous breathing airflow from at least one thermal sensor disposed near or in an entrance of an airway, and wherein a combination of the spontaneous breathing airflow and the tracheal, nasal or oral pressure is used to optimize ventilator synchronization and titration of therapy.

26. A ventilation and breath sensing apparatus comprising:
  a ventilation gas delivery circuit;
  a ventilation tube coupled to the ventilation gas delivery circuit and further defined by a patient airway end;
  a plurality of breath sensing elements disposed on the patient airway end of the ventilation tube
  including at least one pressure sensing port to directly measure airway breathing pressure to determine true breathing activity of a patient, and at least one thermal sensor, airflow through a patient airway being derived from measurements of the at least one thermal sensor;
  wherein control over at least one of ventilation gas delivery timing, amplitude, speed, waveform shape, frequency, and composition is based upon a correlated combination of the signals from the breath sensing elements and the derived airflow to adapt to the true breathing activity of the patient.

27. The ventilation and breath sensing apparatus of claim 26, further comprising at least two thermal sensors coupled in an array.

28. A ventilation and breath sensing apparatus comprising:
  a ventilation interface tube with a gas delivery conduit,
  at least one breath sensing channel not connected to and parallel to the gas delivery channel and having an opening in communication within an airway of the patient to directly measure airway pressures, and
  a first sensor and a second sensor in the at least one breath sensing conduit;
  wherein the first sensor produces a first signal;
  wherein the second sensor produces a second signal;
  wherein the second sensor is at a distance from the first sensor and producing a signal independent from the first signal; a processor for calculating (1) a pressure differential between the first signal and the second signal, (2) at least one of a tracheal, nasal and oral pressure derived from the pressure differential between the first signal and the second signal, and (3) at least one of a tracheal, nasal and oral air flow derived from the respective tracheal, nasal, and oral pressure representative of a true breathing activity of the patient; and wherein the processor initiates ventilation based upon a combination of at least one of the tracheal, nasal and oral air flow and at least one of the tracheal, nasal, and oral pressure.

29. The ventilation and breath sensing apparatus of claim 28, wherein at least one of the first sensor and the second sensor are pressure sensors.

30. The ventilation and breath sensing apparatus of claim 28, further comprising at least one thermal sensor disposed near or in an entrance of an airway, wherein the at least one thermal sensor is used to determine spontaneous breathing airflow, and wherein a combination of the spontaneous breathing airflow and the tracheal, nasal or oral pressure is used to optimize ventilator synchronization and titration of therapy.

* * * * *